United States Patent [19]

Nishi et al.

[11] Patent Number: 4,868,125
[45] Date of Patent: Sep. 19, 1989

[54] PROMOTER

[75] Inventors: Tatsunari Nishi, Tokyo; Akiko Saito, Machida; Seiga Itoh, Sagamihara, all of Japan

[73] Assignee: Kyowa Hakko Kogyo Co., Ltd., Tokyo, Japan

[21] Appl. No.: 113,435

[22] Filed: Oct. 28, 1987

Related U.S. Application Data

[63] Continuation of Ser. No. 681,292, Dec. 13, 1984, abandoned.

[30] Foreign Application Priority Data

Dec. 21, 1983 [JP] Japan ................... 58-241134

[51] Int. Cl.$^4$ ................. C12N 1/00; C12N 15/00; C12N 1/20
[52] U.S. Cl. .................. 435/320; 435/172.3; 435/252.33; 935/41
[58] Field of Search ............... 435/172.3, 320; 935/41

[56] References Cited

U.S. PATENT DOCUMENTS 4,551,433 11/1985 DeBoer ..................... 435/172.3

FOREIGN PATENT DOCUMENTS 0067540 12/1982 European Pat. Off. .

OTHER PUBLICATIONS

De Boer et al., Promoters, Structure and Function, edited by Rodriguez et al., Praeger Pub. pp. 462–481 (1982).
Horn et al., The Journal of Biological Chemistry, vol. 256, pp. 1998–2002, 2003–2009, Feb. 25, 1981.
Chem. Abs., vol. 100, No. 23 (1984) 186664f.
Chem. Abs., vol. 98, No. 11 (1983) 84359h.
Proc. Miami Wint. Symp., vol. 19 (1982) 309:27.
De Boer et al., PNAS, USA, vol. 80, pp. 21–25, Jan. 1983.
Klein et al., Jr. Biol. Chem., vol. 257, pp. 12954–12961, Nov. 1982.
Royama et al., Nucleii Acids Research, vol. 11, pp. 5855–5864, Sep. 10, 1983.
Berman et al., PNAS, USA, vol. 76, pp. 4303–4307, Sep. 1979.
Stefano et al., PNAS, USA, vol. 79, pp. 1069–1072 (1982).

Primary Examiner—Alvin E. Tanenholtz
Attorney, Agent, or Firm—Fitzpatrick, Cella, Harper & Scinto

[57] ABSTRACT

Disclosed is a novel promoter wherein a 5' flanking region of a promoter (referred to as promoter A hereinafter) is replaced with a 5' flanking region of another promoter (referred to as promoter B hereinafter) or a chemically synthesized DNA fragment. The promoter is constructed by replacing a region existing upstream from the "−35" region of promoter A with the "−35" region of promoter B or a chemically synthesized DNA fragment.

2 Claims, 9 Drawing Sheets

PROMOTER

This application is a continuation of application Ser. No. 681,292, filed Dec. 13, 1984, now abandoned.

BACKGROUND OF THE INVENTION

By the development of recombinant DNA technique in recent years, mass production of heterogeneous proteins has become possible using microorganisms, particularly *Escherichia coli.*

Improvement of the frequency of expression of heterogeneous genes in host cells is an important subject.

Specifically, in order to elevate transcription efficiency, as the promoter which is genetic information necessary for the initiation of transcription, lactose (lac) promoter (referred to as lac promoter hereinafter), tryptophan (trp) promoter (referred to as trp promoter hereinafter) and the like have been employed. Further, a hybrid promoter (tac promoter) of trp promoter and lac promoter has been designed. They are employed for expression of heterogeneous genes [K. Itakura, et al.: Science 198, 1056-1063(1977), D. V. Goeddel, et al.: Nature 287, 411-416 (1980), H. A. deBoer, et al.: Proc. Natl. Acad. Sci. USA, 80, 21-25 (1983)].

The region which RNA polymerase recognizes and binds to initiate transcription is named "promoter". It is well known that transcription efficiency depends on the DNA base sequence of the "promoter". According to the conventional numbering system of DNA base sequences, the promoter of *Escherichia coli* comprises the region around "−35", which is usually named "−35" region, the region around "−10", which is named "−10" region or Pribnow box, and the region of "+1", i.e. transcription initiation site which is a purine base such as adenine and guanine in most promoters. "−35" region is defined as a recognition site of RNA polymerase. According to the statistical analysis of base sequences of various *Escherichia coli* promoters, it is clarified that the consensus sequence is TGTTGACANTTT wherein A is adenine, T is thymine, G is guanine, C is cytosine and N is any of A, T, G and C. The most frequently appearing part of the consensus sequence is TTGACA. On the other hand, "−10" region is recognized as an RNA polymerase binding site and the consensus sequence thereof is TATAATG [M. Rosenberg & D. Court: Ann. Rev. Genet. 13. 319 (1979)].

As the promoters generally used to express a gene of eukaryotes, lac UV5 promoter [F. Fuller: Gene 19, 43 (1982)], trp promoter [G. N. Bennet, et al.: J. Mol. Biol. 121, 113 (1978): D. V. Goeddel, et al.: Nature 287, 411 (1980)] are known. In the case of lac UV5 promoter, the "−10" region (TATAATG) is completely identical with the consensus sequence of "−10" region of *Escherichia coli* promoter described above but the "−35" region (GCTTTACACTTT) is not identical with the consensus sequence. Reversely, in the case of trp promoter, the "−35" region (TGTTGACAATTA) is almost identical with the consensus sequence but the "−10" region (TTAACTA) is not identical with the consensus sequence.

H. A. deBoer, et al. of Genentech Inc. constructed a hybrid promoter by ligating a DNA fragment containing "−35" region of trp promoter and the 5' flanking region upstream therefrom and a DNA fragment containing "−10" region of lac promoter and lac operator, utilizing superiority of trp promoter and lac UV5 promoter. The hybrid promoter was named tac promoter and has been employed to express human growth hormone. The tac promoter is characterized in that "−35" region derived from trp promoter and "−10" region derived from lac promoter are constructed so as to function as a promoter and both regions are almost identical with the consensus sequences [H. A. deBoer, et al.: Proc. Natl. Acad. Sci. USA 80, 21 (1983)].

The thus constructed tac promoter was proved to have transcription activity which is about 3.5 times stronger than that of trp promoter and 2-3 times stronger than that of lac promoter. Further, H. A. deBoer, et al. constructed rac promoter which is a hybrid promoter of the promoter of ribosome RNA operon known as an extremely strong promoter and lac promoter to use for expression of human growth hormone (Japanese Published Unexamined Patent Application No. 194790/82).

Thus H. A. deBoer, et al. provided a method of constructing novel hybrid promoters by religating selectively and functionally the DNA fragment containing 5' flanking region and "−35" region and the DNA fragment containing "−10" region utilizing superiority of the two promoters. The method may be useful for the construction of hybrid promoters which have a strong transcription activity and an ability to control expression. However, the method is not adequate to construct promoters which can maximally exhibit the transcription ability of *Escherichia coli*. The present inventors have studied to elevate the transcription activity of trp promoter and tac promoter.

H. A. deBoer et al. reported the following factors affecting the strength of promoter [H. A. deBoer, et al.: "Promoters: structure and function" R. L. Rodriguez, et al. M. J. Chamberlin ed. (Praeger Co.) 462-481 (1982)]:

(1) Base sequence of "−10" region
(2) Base sequence of "−35" region
(3) Distance between "−10" and "−35" regions
(4) AT content in 5' flanking region upstream from "−35" region
(5) Appropriate combination of these factors Factors (1),(2) and (3) are known to have an important effect on the strength of a promoter. The present inventors presumed that the factor (4) would have an important effect on the strength of a promoter.

Some strong *Escherichia coli* promoters are known to be abundant with adenine (A) and thymine (T) in the 5' flanking region and to contain a part (AT) wherein A and T are linked successively. [Z. Humayun, et al.: J. Mol. Biol. 112, 265 (1977), G. T. Horn, et al.: J. Biol. Chem. 256, 1998 (1981), G. N. Bennet, et al.: J. Mol. Biol. 121, 113 (1978), K. Nakamura, et al.: Cell 18, 1109 (1979)].

Further, it is known that the AT content in the 5' flanking region affects the strength of a promoter. That is, G. T. Horn, et al. reported that the strength of $P_L$ promoter of λ phage was reduced by the deletion of the 5' flanking region abundant with AT [G. T. Horn, et al.: J. Biol. Chem. 256, 2003 (1981)]. Further, R. D. Klein, et al. reported that the in vitro transcription activity of lac promoter was enhanced by inserting a double stranded DNA poly(A)·poly(T) of about 70 bp into the site upstream from the "−35" region of lac promoter [J. Biol. Chem. 257, 12954 (1982)]. Therefore, it is presumable that endowment of a sequence abundant with AT to 5' flanking region increases the strength of a promoter.

The 5' flanking region of $P_L$ promoter has the following characteristics (refer to Table 1). First of all, two parts abundant with AT are included in the 5' flanking region. The two parts abundant with AT are −186 to −155 and −101 to −75 according to the conventional numbering wherein the transcription initiation site of $P_L$ promoter is indicated by +1.

upstream from the "−35" region of an *Escherichia coli* promoter or an artificially constructed promoter (both referred to as promoter A hereinafter) with the "−35" region of another promoter (referred to as promoter B hereinafter) or a chemically synthesized DNA fragment.

TABLE 1

DNA base sequence of $P_L$ promoter

```
         Hpa II                 Pvu I
  C|CGGGTTTTCTTTGCCTCACGAT|CGCCCCCAAAACACATAACCAATTGTATTTATTGAAA
       ↓                      ↓
                                     Region abundant with AT Bgl II
  AATAAATAGATACAACTCACTAAACATAGCAATTCA|GATCTCTCACCTACCAAACAATGC
                                          ↓

CCCCCTGCAAAAAATAAATTCATATAAAAAACATACAGATAACCATCTGCGGTGATAAAT
         Region abundant with AT                "35"-like sequence
                                                    −1+1
         Hinc II
  TATCTCTGGCGGTGTT|GACATAAATACCACTGGCGGTGATACTGAGCACATCAGCAGGAC
                  ↓                  "−10" region         mRNA
            "−35" region
```

G. T. Horn, et al. reported that the deletion of both AT-abundant parts resulted in reduction of the strength of $P_L$ promoter but did not change the function of $P_L$ promoter [G. T. Horn, et al.: J. Biol Chem., 256, 2003 (1981)]. A "−35"-like base sequence present in the part from −60 to −49 also may have relation to the strength of the promoter. In the case of the base sequence of $P_L$ promoter, the sequences of "−35" region and "−10" region are very similar to but not identical with the respective consensus sequences. The similarity of the sequences to the consensus sequences is in the same degree with that in the case of trp promoter. However, $P_L$ promoter has a stronger transcription activity than trp promoter. This may be caused by the difference of the base sequences in the 5' flanking regions. Therefore, a promoter wherein the 5' flanking region is replaced with that of $P_L$ promoter may be strengthened.

In order to replace 5' flanking region, the method developed by H. A. deBoer, et al., that is, the method which comprises recombining "−35" region containing 5' flanking region and "−10" region to construct a new hybrid promoter (Japanese Published Unexamined Patent Application No. 194790/82) is applicable. However, the method has a possibility to impair the function inherited by a promoter since the recombination of "−35" region and "−10" region is variable. For example, when the method is applied to very excellent tac promoter to construct a stronger promoter by replacing the 5' flanking region with another one, the 5' flanking region and the "−35" region are liable to be simultaneously replaced with other DNA fragments, whereby the "−35" region inherent in tac promoter is lost.

The present inventors have found a process for replacing only the 5' flanking region as described hereinafter, that is, a process for replacing only the 5' flanking region utilizing a restriction site which is present around or upstream from the "−35" region.

SUMMARY OF THE INVENTION

The present invention relates to a novel promoter which is strengthened in transcription activity. More specifically, this invention relates to a novel promoter which is constructed by replacing a region existing

DETAILED DESCRIPTION OF THE INVENTION

Figure 1:
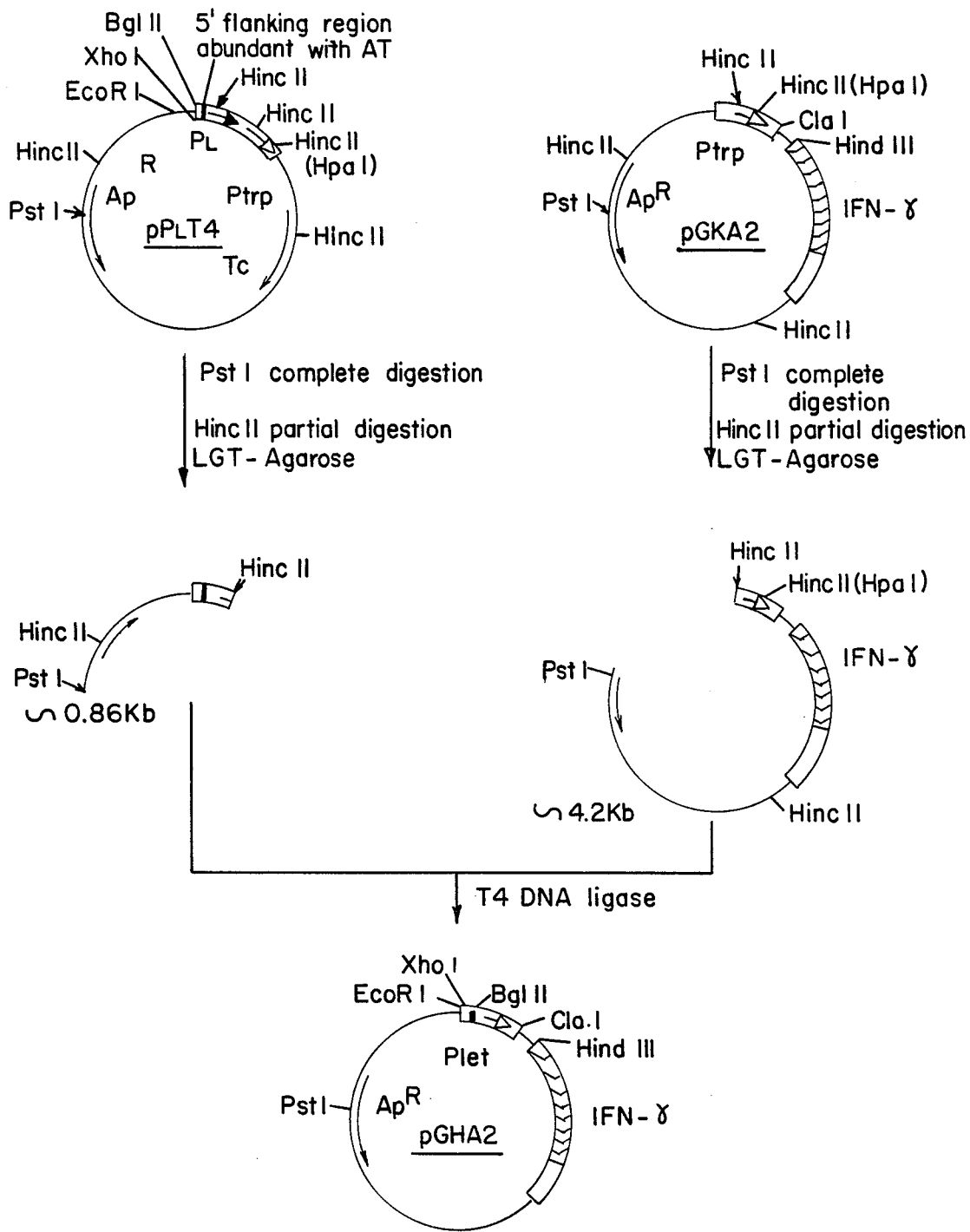
FIG. 1. illustrates the process for constructing pGHA2.

The present invention provides a novel promoter wherein the 5' flanking region of a promoter (referred to as promoter A hereinafter) is replaced with the 5' flanking region of another promoter (referred to as promoter B hereinafter) or a chemically synthesized DNA fragment.

As examples of promoter A, *Escherichia coli*- derived promoters such as the promoter of tryptophan (trp) operon (trp promoter) and the promoter of lactose (lac) operon (lac promoter), tac promoter which is a hybrid promoter of trp promoter and lac promoter and artificially constructed promoters are mentioned.

As promoter B, a promoter which has a stronger transcription activity than promoter A is preferably used. However, a promoter which has a transcription activity equivalent to or weaker than promoter A is applicable since the transcription activity may be enhanced by replacement.

As examples of promoter B, *Escherichia coli*- derived promoters such as $P_L$ promoter of λ phage, $P_R$ promoter of λ phage, ribosome RNA (rrn) promoter, lipoprotein gene promoter, and the like are mentioned.

Replacement of 5' flanking region of promoter A with 5' flanking region of promoter B or a chemically synthesized DNA fragment is carried out using a restriction site around or upstream from "−35" region of promoter A or an appropriate restriction site in "−35" region or 5' flanking region. In the case of using the restriction site in "−35" region, a restriction site should be selected so as not to convert the base sequence of "−35" region by replacement. Further, it is possible to insert 5' flanking region of promoter B or a chemically synthesized DNA fragment after removing 5' flanking region of promoter A using a nuclease such as BAL31.

As the 5' flanking region of promoter A, for example, regions cut out by the following restriction enzymes are mentioned.

| Promoter A | 5' flanking region |
|---|---|
| trp promoter | HincII, HhaI |
| lac promoter | AluI |
| tac promoter | HincII, HhaI |

As the 5' flanking region of promoter B, regions cut out by the following restriction enzymes are mentioned.

| Promoter B | 5' flanking region |
|---|---|
| $P_L$ promoter | HincII, BglII, PvuI, HpaII |
| $P_R$ promoter | HincII |
| rrn promoter | HaeIII |
| lipoprotein gene promoter | Sau3A, TaqI |

As the 5' flanking region of promoter B and chemically synthesized DNA fragments, regions and DNA fragments abundant with AT are preferably used.

The present invention is explained more in detail referring to the case of replacement of 5' flanking region of very strong $P_L$ promoter with that of trp promoter or tac promoter.

As apparent from Table 1, $P_L$ promoter contains HincII site in "−35" region. As apparent from Tables 2 and 3, trp promoter and tac promoter contain HincII site in "−35" region at the same position as the HincII site in $P_L$ promoter.

TABLE 2

DNA base sequence of the trp promoter region of pKYP10

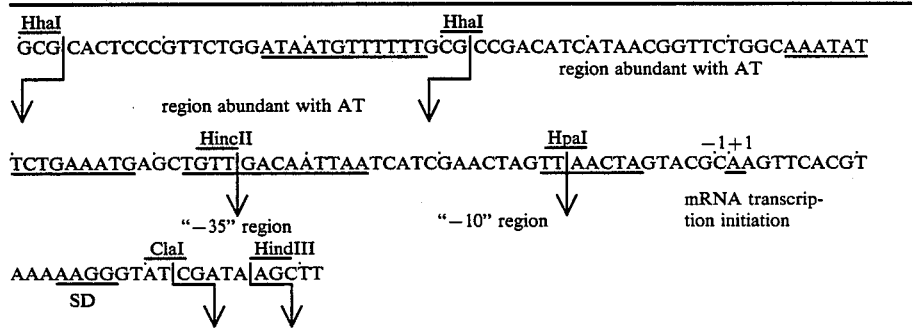

TABLE 3

DNA base sequence of the tacI promoter region of pTAC10

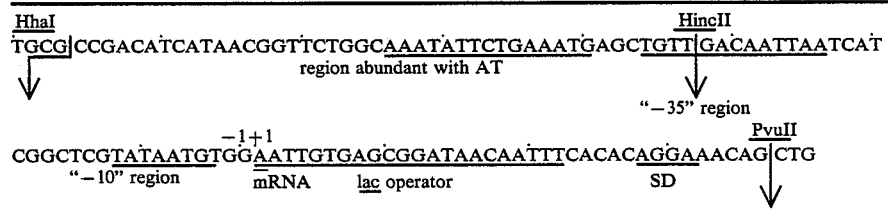

Therefore, using these HincII sites, a novel promoter wherein a region upstream from HincII site of $P_L$ promoter is replaced with a region downstream from HincII site of trp of tac promoter can be constructed (refer to Tables 4 and 5).

TABLE 4

DNA base sequence of the let promoter of pGHA2

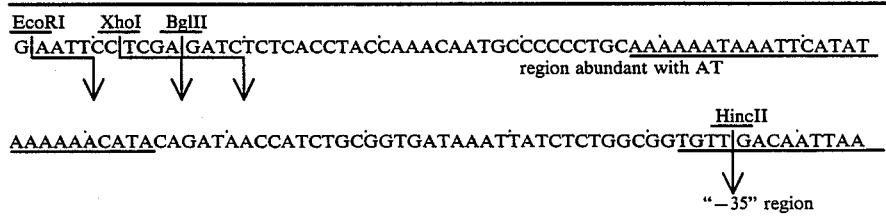

TABLE 4-continued

DNA base sequence of the let promoter of pGHA2

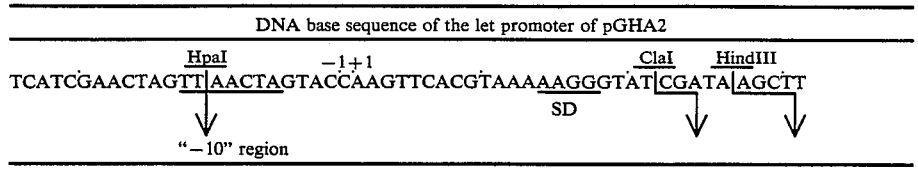

TABLE 5

DNA base sequence of the lecI promoter of pLECl

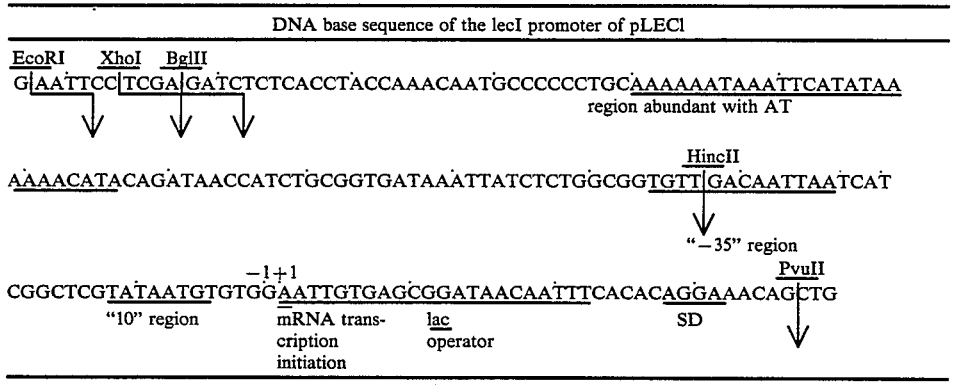

These novel promoters are named let (leftward promoter+trp promoter) promoter and lec (leftward promoter+tac promoter) promoter, respectively. Let and lec promoters are constructed using HincII site in "−35" region without any change of the base sequences in "−35" region. Therefore, it is possible to enhance the transcription activity without imparing the function of original trp and tac promoters. In fact, as described below, let promoter has a transcription activity about 10 times stronger than that of trp promoter and lec promoter has a transcription activity about twice stronger than that of tac promoter. Both trp promoter and tac promoter contain a part abundant with AT in the 5' flanking region (refer to Tables 2 and 3). Nevertheless, the transcription activity of trp and tac promoters is increased by replacing their 5' flanking regions with that of $P_L$ promoter. This suggests that a specific base sequence, in addition to the AT content in the 5' flanking region of $P_L$ promoter, contributes to the increase of transcription activity.

Figure 5:
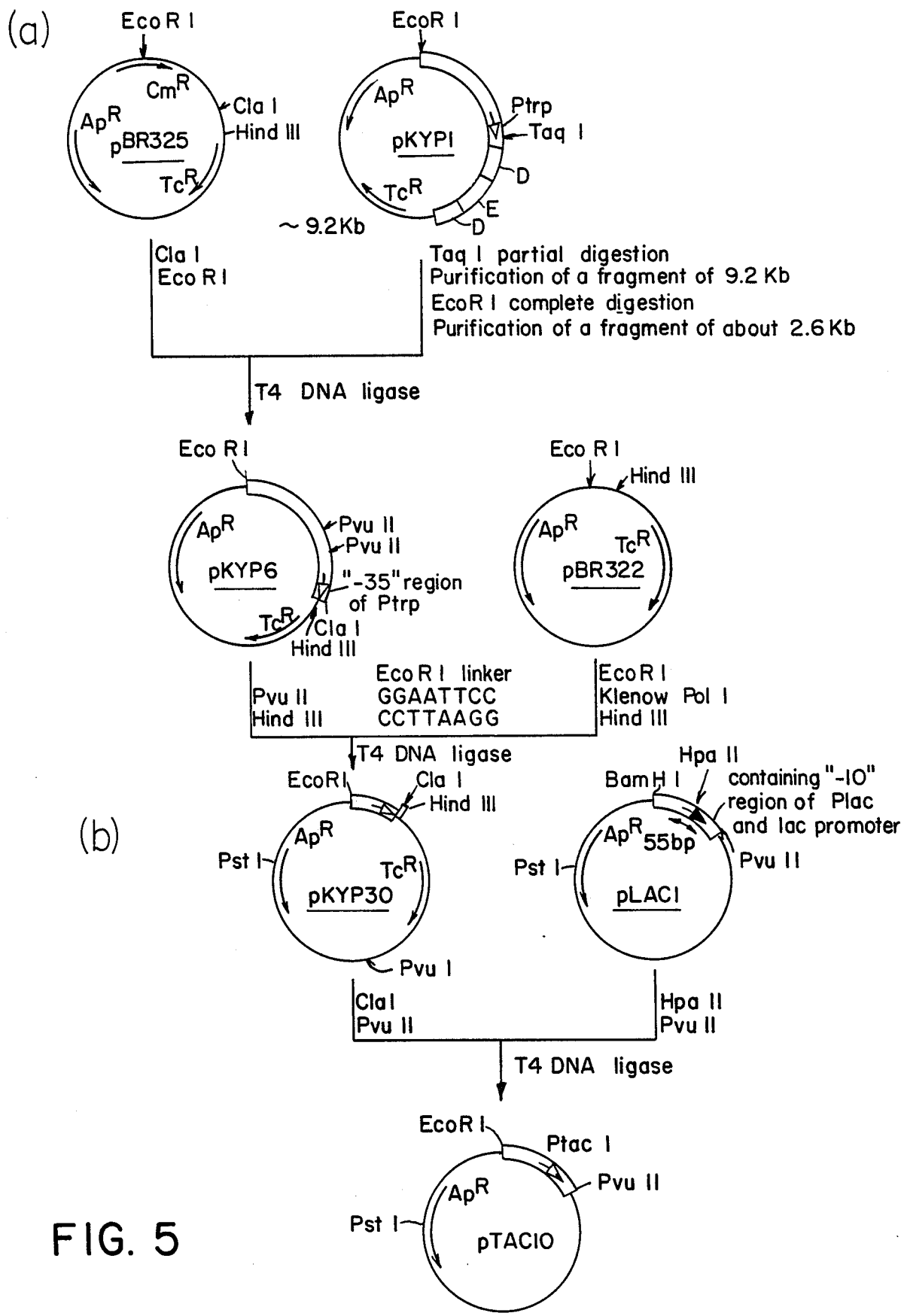
FIG. 5. illustrates the process for constructing pTAC10.

Thus, only 5' flanking region can be replaced using a restriction site around or upstream from "−35" region. Such replacement can also be carried out using other methods. For example, in the case of replacing 5' flanking region of tac promoter with that region of $P_L$ promoter, the desired promoter like lec promoter can be constructed by removing 5' flanking region by digestion with an exonuclease such as BAL31 from an appropriate restriction site upstream from tac promoter, for example, EcoRI site of pTAC10 illustrated in FIG. 5, and inserting a DNA fragment containing 5' flanking region of $P_L$ promoter. Further, it is possible to construct a promoter strengthened in transcription activity by inserting 5' flanking region of another promoter or a chemically synthesized DNA fragment abundant with AT into a restriction site upstream from "−35" region.

Chemical synthesis of DNA fragments is carried out according to the method described in M. Ito, et al.: Nucleic Acids Res. 10, 1775 (1982).

Reaction conditions required for preparing the recombinant plasmid carrying the promoters described above are as follows.

Digestion of the DNA with restriction enzymes is usually carried out by reacting 0.1 to 20 μg of DNA with 0.1-100 units, preferably 1-3 units of restriction enzyme per 1 μg of DNA in a mixture of 2-200 mM, preferably 10-40 mM Tris-HCl (pH 6.0-9.5, preferably pH 7.0-8.0), 0-200 mM NaCl and 2-20 mM, preferably 5-10 mM MgCl$_2$ at 20°-70° C. (optimal temperature depends on restriction enzymes used) for 15 minutes to 24 hours. Reaction is usually stopped by heating at 55°-75° C. for 5-30 minutes, or alternatively by inactivating the restriction enzyme with the reagent such as phenol or diethylpyrocarbonate. In the case where purification of DNA fragment formed by digestion with restriction enzymes is necessary, low-gelling-temperature agarose gel electrophoresis [L. Wieslander: Analytical Biochemistry 98, 305 (1979)] or polyacrylamide gel electrophoresis [A. M. Maxam, et al.: Proc. Natl. Acad. Sci. USA 74, 560 (1977)] is employed for the purification.

Ligation of the DNA fragments is carried out with 0.3-10 units of T4DNA ligase in a mixture of 2-200 mM, preferably 10-40 mM Tris-HCl (pH 6.0-9.5, preferably 7.0-8.0), 2-20 mM, preferably 5-10 mM MgCl$_2$, 0.1-10 mM, preferably 0.5-2.0 mM ATP and 1-50 mM, preferably 5-10 mM dithiothreitol at 1°-37° C., preferably 3°-20° C. for 15 minutes to 72 hours, preferably 2-20 hours. In the case where the thus formed recombinant plasmid DNA is required to be introduced into Escherichia coli, the plasmid DNA can be introduced by the transformation method of Cohen, et al. [S. N. Cohen, et al.: Proc. Natl. Acad. Sci. USA 69, 2110 (1972)]. In the case where the recombinant plasmid DNA is required to be isolated from Escherichia coli carrying the DNA, the method described in Example 1 or the method of Birnboim, et al. [H. C. Birnboim, et al.: Nucleic Acids Res. 7, 1513 (1979)] may be employed. The structure of the isolated DNA is analyzed in the following manner. Plasmid DNA is digested with 1-10 kinds of restriction endonucleases and the cleavage sites are examined by agarose gel electrophoresis or polyacrylamide gel electrophoresis. Further, if necessary, the base sequence of the DNA is determined by the method of Maxam-Gilbert [A. M. Maxam, et al.: Proc. Natl. Acad. Sci. USA 74, 560 (1977)].

Recombinant plasmid DNAs can be produced by the method described above.

Certain specific embodiments of the present invention are illustrated by the following examples.

EXAMPLE 1

Construction of let promoter and expression of human IFN-γ gene using said promoter Plasmid pP$_L$T4 carrying P$_L$ promoter and constructed in Reference Example 1, and IFN-γ expressing plasmid pGKA2 constructed in Reference Example 3 were recombined by the following method to obtain plasmid pGHA2 which expresses human IFN-γ under the control of let promoter wherein 5' flanking region of trp promoter is replaced with that region of P$_L$ promoter (refer to FIG. 1).

About 10 μg of pP$_L$T4 plasmid DNA (about 4.7 kilobase pairs: referred to as Kb hereinafter) was dissolved in 50 μl of a buffer solution consisting of 10 mM Tris-HCl (pH 7.5), 50 mM NaCl, 7 mM MgCl$_2$ and 6 mM 2-mercaptoethanol (referred to as "Y-50 buffer solution" hereinafter). 20 units of restriction enzyme PstI (product of Takara Shuzo Co., the restriction enzymes hereinafter are all products of Takara Shuzo Co., unless otherwise specified) was added and reaction was carried out at 37° C. for 1 hour. Subsequently, 4 units of HincII was added and reaction was continued for 1 hour. By the reaction, the DNA was digested completely with PstI and partially with HincII. After heat treatment at 65° C. for 10 minutes, purification was carried out by low-gelling-temperature agarose gel electrophoresis [L. Wieslander: Analytical Biochemistry 98, 305 (1979), hereinafter the method is used in the purification of DNA fragments unless otherwise specified] to obtain a PstI-HincII fragment of about 0.86 Kb containing a part of the ampicillin (referred to as Ap hereinafter) resistance gene and the 5' flanking region of P$_L$ promoter.

Separately, about 10 μg of pGKA2 plasmid (about 5.2 Kb, refer to Reference Example 3) expressing human IFN-γ gene under the control of trp promoter was digested with 20 units of PstI in 50 μl of Y-50 buffer solution at 37° C. for 1 hour. Then, 4 units of HincII was added and reaction was continued for 1 hour. By the reaction, the DNA was digested completely with PstI and partially with HincII. After heat treatment at 65° C. for 10 minutes, purification was carried out by low-gelling-temperature agarose gel electrophoresis to obtain a HincII-PstI fragment of about 4.2 Kb containing the most part of the trp promoter, the human IFN gene and a part of the Ap resistance gene.

About 0.05 μg of the PstI-HincII fragment derived from pP$_L$T4 and about 0.05 μg of the HincII-PstI fragment derived from pGKA2 thus obtained were subjected to ligation reaction with 1 unit of T4 DNA ligase, (product of Takara Shuzo Co., the same shall apply hereinafter) at 4° C. for 18 hours in 10 μl of a buffer solution consisting of 20 mM Tris-HCl (pH 7.6), 10 mM MgCl$_2$, 10 mM dithiothreitol and 0.5 mM ATP (referred to as "T4 DNA ligase buffer solution" hereinafter).

Escherichia coli HB101 [F$^{31}$ hsdR hsdM pro leu thi rpsL recA, Boliver, et al., Gene 2 75 (1977)] was transformed with the thus obtained recombinant plasmid DNA by the method of Cohen, et al. [S. N. Cohen, et al.: Proc. Natl. Acad. Sci. USA 69, 2110 (1972), transformation of Escherichia coli is carried out by this method hereinafter] to obtain an Ap resistant strain. Plasmid DNA was isolated from the transformant by the following method.

The transformant was inoculated in 8 ml of LG medium (1.0% Bacto-trypton, 0.5% yeast extract, 0.5% NaCl, 0.1% glucose, pH 7.2) containing 50 μg/ml ampicillin and culturing was carried out at 30° C. for 15-18 hours. The culture liquor was centrifuged at 10,000 rpm for 5 minutes to harvest cells. The cells were suspended in 400 μl of a buffer solution containing 50 mM Tris-HCl (pH 7.5) and 10 mM EDTA and frozen in dry ice-ethanol. After thawing at 20° C., 40 μl of 2.5M KCl and 40 μl of 5 mg/ml lysozyme suspension in the buffer solution mentioned above were added and the mixture was allowed to stand in ice for 15 minutes. Freezing and thawing mentioned above were repeated and centrifugation was carried out at 15,000 rpm for 20 minutes to recover a supernatant fluid. The supernatant was extracted with a mixture solution of phenol and chloroform and twice as much ethanol as the extract by volume was added to precipitate DNA. The DNA fragment was collected by centrifugation and suspended in 50-100 μl of a solution of 10 mM Tris-HCl (pH 7.5) and 1 mM EDTA containing 50 μg/ml RNase A (product of Sigma) to prepare partially purified plasmid DNA (this method is used for isolation of plasmid DNAs hereinafter). The structure of the plasmid DNA isolated was analyzed to recognize that plasmid pGHA2 in IGHA2 had the desired structure.

In pGHA2, human IFN-γ gene is ligated upstream from the let promoter constructed by replacing the 5' flanking region of trp promoter with that region of P$_L$ promoter. The base sequence between Shine-Dalgarno sequence (referred to as SD sequence hereinafter) derived from trpL gene and the ATG initiation codon of IFN-γ gene is the same as that of pGKA2 (AAGG-GTATCGATAAGCTTATG). The base sequence of the let promoter newly constructed is illustrated in Table 4. As illustrated in Table 4, the let promoter has the form of the portable promoter which is cut out with EcoRI (or XhoI, or BglII) and ClaI (or HindIII).

Escherichia coli HB101 carrying recombinant plasmid pGKA2 (IGKA2) and Escherichia coli HB101 carrying pGHA2 (IGHA2) were tested for interferon production by the following method.

A loopful of the above strains was inoculated in 10 ml of MCG medium (0.6% Na$_2$HPO$_4$, 0.3% KH$_2$PO$_4$, 0.5% NaCl, 0.1% NH$_4$Cl, 0.5% glucose, 0.5% casamino acid, 1 mM MgSO$_4$, 4 μg/ml thiamine hydrochloride, pH 7.2) and culturing was carried out at 30° C. for 17 hours. The culture broth was centrifuged at 8,000 rpm for 10 minutes to collect cells. The cells were washed with a buffer solution consisting of 30 mM NaCl and 30 mM Tris-HCl (pH 7.5). The washed cells were suspended in 675 μl of PBS buffer solution [0.8% NaCl, 0.02% KCl, 0.115% Na$_2$HPO$_4$, 0.02% KH$_2$PO$_4$ (pH 7.4)]. 25 μl of 0.25 M EDTA and 100 μl of 100 mg/ml lysozyme solution in distilled water were added and the mixture was allowed to stand at 0° C. for 30 minutes. Then, 200 μl of 5M NaCl-5% polyethyleneglycol #1000 was added. Freezing and thawing were repeated three times to disrupt cells. The disrupted cells were centrifuged at 15,000 rpm for 30 minutes to recover a supernatant fluid. The amount of interferon in the supernatant was determined by the method of Armstrong [J. A. Armstrong: Appl. Microbiol. 21, 723-725 (1971)] wherein Sindvis virus was used as a virus and FL cell derived from human amnion cells was used as animal cells.

As the result of the measurement of interferon activity, it was found that IGKA2 carrying pGKA2 plasmid which expresses IFN-γ gene under the control of the trp promoter produced about $5 \times 10^6$ units/l interferon and IGHA2 carrying pGHA2 plasmid which expresses IFN-γ gene under the control of the let promoter produced about $5 \times 10^7$ units/l interferon. In view of the fact that plasmids pGKA2 and pGHA2 have the same structure except for the promoter region, it is apparent that the let promoter wherein the 5' flanking region of the trp promoter is replaced with that of the $P_L$ promoter has transcription activity which is about 10 times stronger than that of the trp promoter. This shows also that the 5' flanking region of the promoter has a very important effect on the transcription activity.

*Escherichia coli* strains carrying pGKA2 and pGHA2 have been deposited with the Fermentation Research Institute, Agency of Industrial Science and Technology (FERM) as *Escherichia coli* IGKA2 (FERM P-6798) and IGHA2 (FERM BP-400), respectively.

EXAMPLE 2

Construction of lecI promoter

Figure 2:
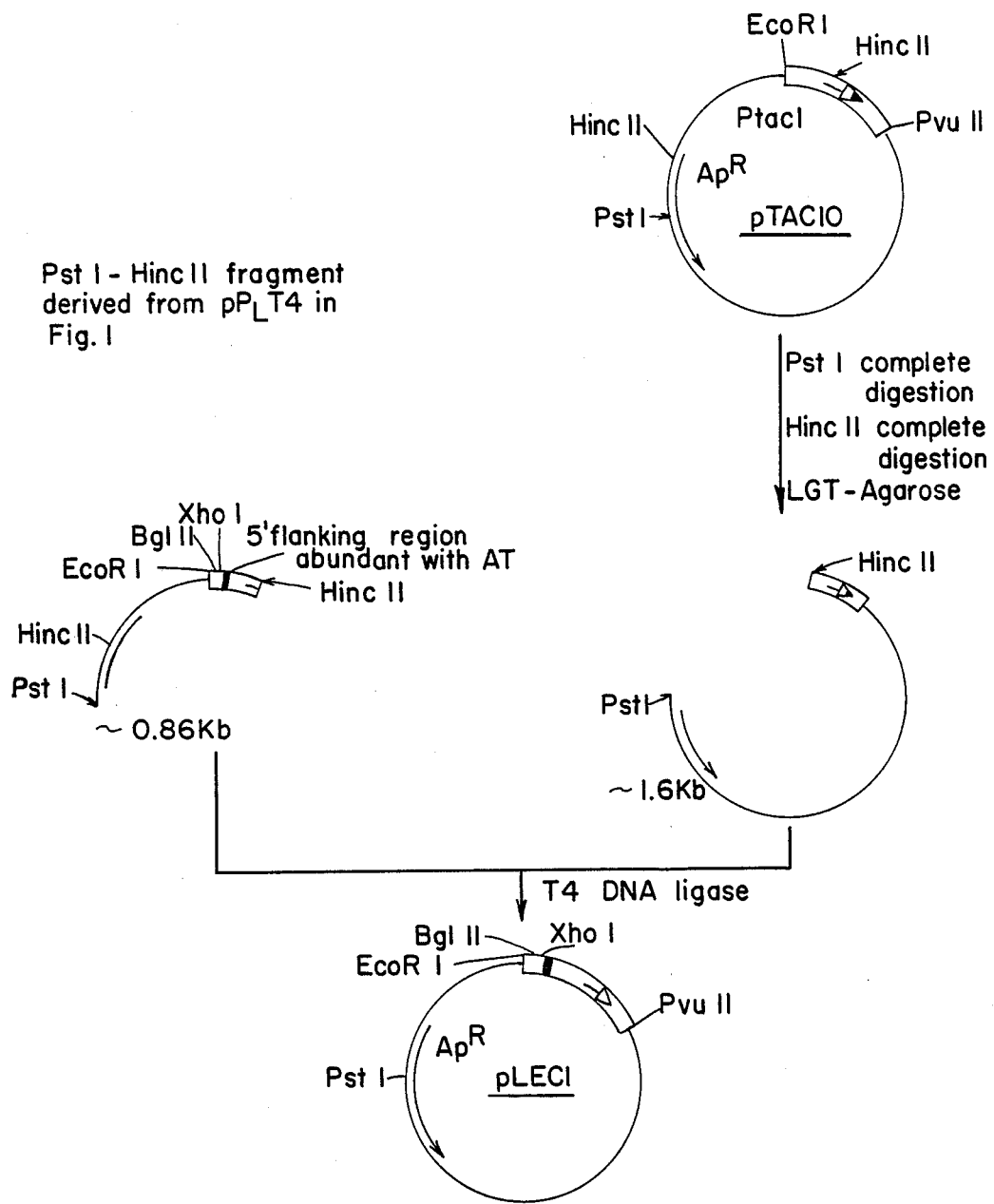
FIG. 2. illustrates the process for constructing pLEC1.

Plasmid p$P_L$T4 carrying $P_L$ promoter and constructed in Reference Example I, and plasmid pTAC10 carrying tacI promoter and constructed in Reference Example 2 were recombined by the following method to construct plasmid pLECl carrying lecI promoter wherein the 5' flanking region of the tacI promoter was replaced (refer to FIG. 2).

About 5 μg of pTAC10 plasmid carrying the tacI promoter (about 2.6 Kb, refer to Reference Example 2) was digested with 10 units of PstI and 10 units of HincII in 50 μl of Y-50 buffer solution at 37° C. for 2 hours. After heat treatment at 65° C. for 10 minutes, purification was carried out by low-gelling-temperature agarose gel electrophoresis to obtain a HincII-PstI fragment of about 1.6 Kb containing the most part of the tacI promoter and a part of the Ap resistance gene.

About 0.05 μg of the HincII-PstI fragment derived from pTAC10 and obtained as above, and about 0.05 μg of the PstI-HincII fragment derived from p$P_L$T4 and purified in Example 1 were ligated at 4° C. for 18 hours with 1 unit of T4 DNA ligase in 10 μl of T4 DNA ligase buffer solution.

*Escherichia coli* JA221 [F− hsdR hsdM+− trpE5 leu lacY recAl/F' lac I$^q$ lac+ pro+] (FERM BP-405) was transformed with the thus obtained recombinant plasmid DNA to obtain an Ap resistant strain. Plasmid DNA was isolated from the transformant and the structure thereof was analyzed to recognize that plasmid pLECI in ILECI had the desired structure. The lecI promoter in pLECI is a promoter wherein the 5' flanking region of the tacI promoter was replaced with that region of the $P_L$ promoter. The DNA sequence of the lecI promoter is illustrated in Table 5. Since the lecI promoter has PvuII site 5 base pairs (referred to as bp hereinafter) apart downstream from the SD sequence derived from lacZ gene, insertion of a foreign gene and adjustment of the distance between the SD sequence and ATG initiation codon can readily be made.

*Escherichia coli* strain carrying pLECI has been deposited with the FERM as *Escherichia coli* ILECI (FERM BP-401).

EXAMPLE 3

Expression of human IFN-γ gene by lecI promoter

Figure 3:
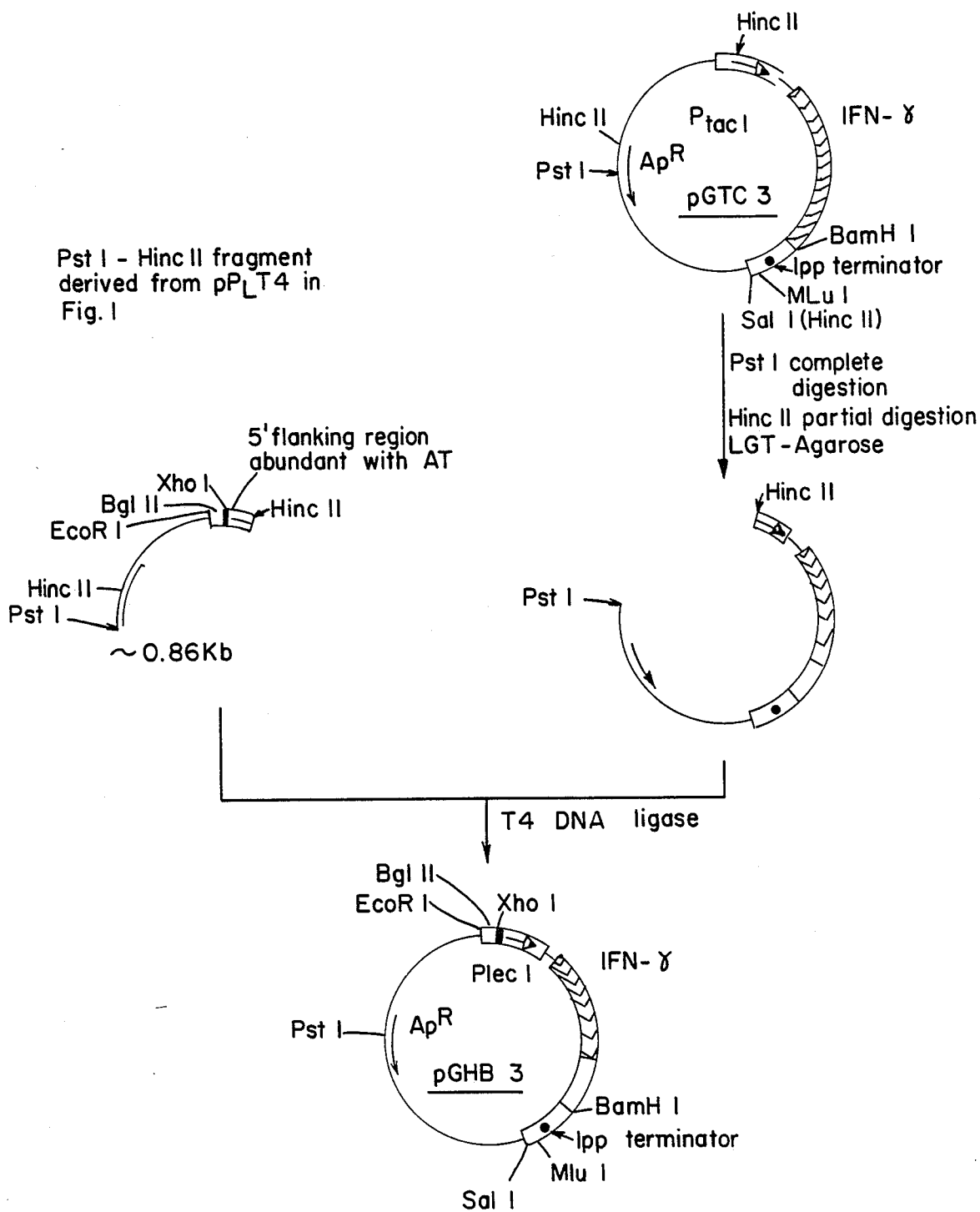
FIG. 3. illustrates the process for constructing pGHB3.

Plasmid pTAC10 carrying the tacI promoter and constructed in Reference Example 2, and plasmid pGTC3 for expression of IFN-γ constructed in Reference Example 4 were recombined by the following method to obtain plasmid pGHB3 which expresses human IFN-γ under the control of lecI promoter wherein the 5' flanking region of the tacI promoter was replaced with that of $P_L$ promoter (refer to FIG. 3).

About 10 μg of pGTC3 plasmid (about 5.15 Kb, refer to Reference Example 4) which expresses human IFN-γ gene under the control of the tacI promoter was digested at 37° C. for 1 hour with 20 units of PstI in 50 μl of Y-50 buffer solution. Then, 4 units of HincII was added and reaction was continued for 1 hour. By the reaction, the DNA was digested completely with PstI and partially with HincII. After heat treatment at 65° C. for 10 minutes, purification was carried out by low-gelling-temperature agarose gel electrophoresis to obtain a HincII-PstI fragment of about 4.2 Kb containing the most part of the tacI promoter, human IFN gene, the translation termination site of lipoprotein gene (referred to as lpp terminator hereinafter) and a part of the Ap resistance gene.

About 0.05 μg of the thus obtained HincII-PstI fragment derived from pGTC3 and about 0.05 μg of the PstI-HincII fragment derived from p$P_L$T4 and purified in Example 1 were ligated with 1 unit of T4 DNA ligase at 4° C. for 18 hours in 10 μl of T4 DNA ligase buffer solution.

*Escherichia coli* JA221 was transformed with the thus obtained recombinant plasmid DNA to obtain an Ap resistant strain. Plasmid DNA was isolated from the transformant and the structure thereof was analyzed to recognize that plasmid pGHB3 in IGHB3 had the desired structure.

In pGHB3, human IFN-γ gene is ligaled downstream from the lecI promoter constructed by replacing the 5' flanking region of the tacI promoter with that region of the $P_L$ promoter. The base sequence between the SD sequence derived from lacZ gene and the ATG initiation codon of IFN-γ gene is the same as that of pGTC3 (AGGAAACAGAGCTTATG).

Then, *Escherichia coli* JA221 carrying recombinant plasmid pGTC3 (IGTC3) and *Escherichia coli* JA221 carrying pGHB3 (IGHB3) were tested for interferon production by the following method.

The strains were inoculated in 5 ml of LG medium [1% Bacto-trypton, 0.5% yeast extract, 0.5% NaCl, 0.1% glucose, pH 7.2] and culturing was carried out overnight. 0.5 ml of the culture broth was inoculated in 10 ml of MCG medium containing 50 μg/ml tryptophan and culturing was carried out at 30° C. When OD$_{550}$ was about 1.0, 1 mM isopropyl β-D-thiogalactoside (referred to as IPTG hereinafter) was added and culturing was continued for about 4 hours. Cells were harvested and interferon activity in the cell was determined by the method described in Example 1.

As the result of the measurement of interferon activity, it was found that IGTC strain carrying pGTC3 plasmid which expresses IFN-γ gene under the control of the tacI promoter produced about $2 \times 10^7$ units/l interferon and IGHB3 strain carrying pGHB3 plasmid which expresses IFN-γ gene under the control of the lecI promoter produced about $4 \times 10^7$ units/l interferon.

In view of the fact that plasmids pGTC3 and pGHB3 have the same structure except for the promoter region, it is apparent that the lecI promoter wherein the 5' flanking region of the tacI promoter was replaced with that of the $P_L$ promoter has transcription activity which is about twice stronger than that of the tacI promoter. This shows that the 5' flanking region of the promoter has an effect on its transcription activity as illustrated in Example 1.

*Escherichia coli* strains carrying pGTC3 and pGHB3 have been deposited with the FERM as *Escherichia coli* IGTC3 (FERM BP-402) and IGHB3 (FERM BP-403), respectively.

REFERENCE EXAMPLE 1

Figure 4:
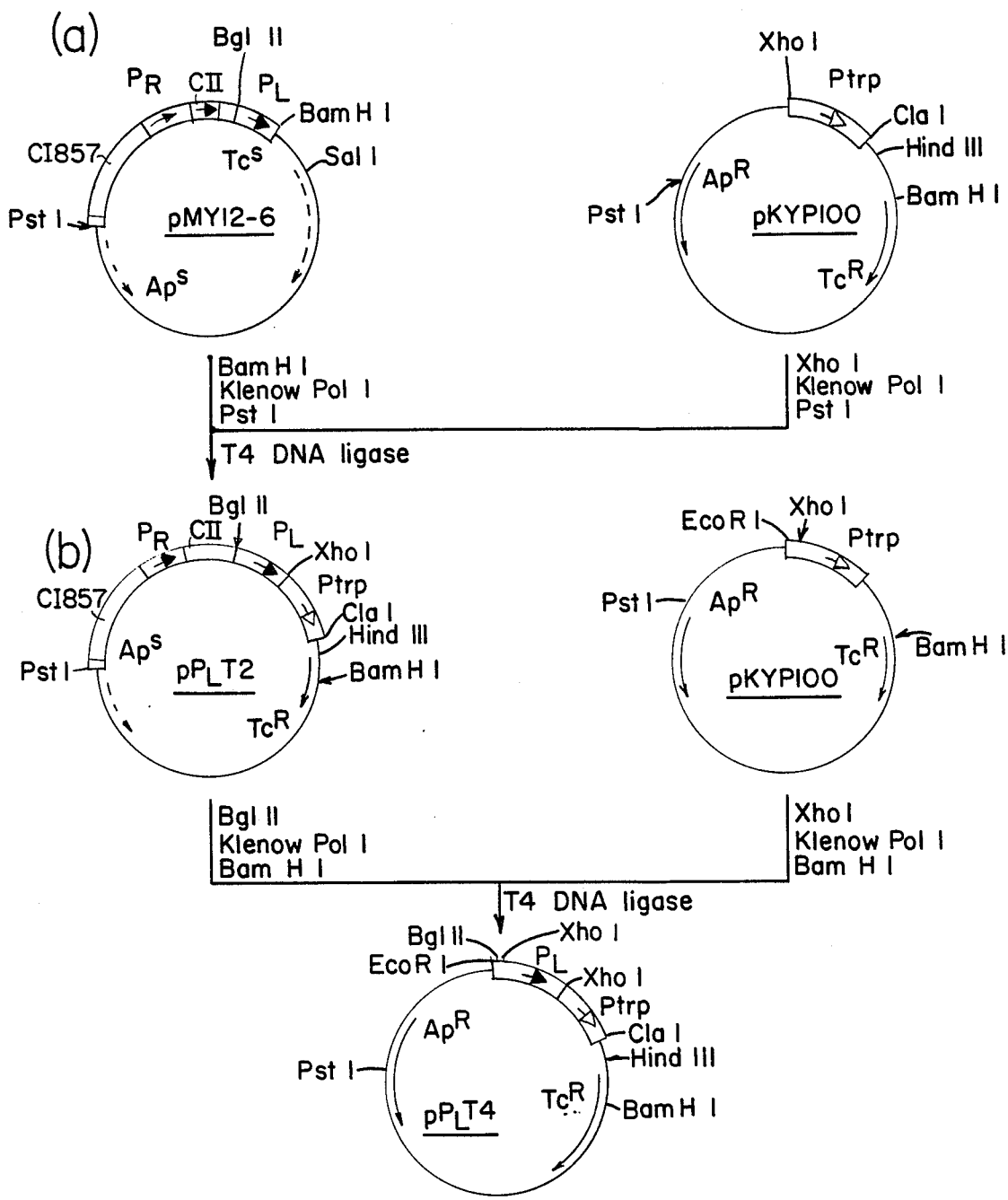
FIG. 4. illustrates the process for constructing pP$_L$T4.

Construction of plasmid vector pP$_L$T4 carrying P$_L$-P$_{trp}$ tandem promoter (refer to FIG. 4)

(a) Construction of pP$_L$T2 carrying P$_R$-P$_L$-P$_{trp}$ tandem promoter

As the source of $P_L$ promoter, plasmid pMY12-6 wherein a DNA fragment derived from λ phage is cloned was used as illustrated in FIG. 4, pMY12-6 has the structure wherein a DNA fragment containing cI gene, $P_R$ promoter and a part of cII gene and derived from λ phage, and a DNA fragment containing $P_L$ promoter and derived from λ phage are inserted between PstI site and BamHI site of plasmid pBR322 [F. Bolivar, et al.: Gene 2, 95 (1977)]. More in detail, according to the numbering of the entire DNA base sequence of λ phage by Sanger, et al. [F. Sanger, et al.: J. Mol. Biol. 162, 729 (1982)], a DNA fragment of 1,350 bp having PstI end and HaeIII end, which is obtained by linking PstIBglII fragment of bases 37,005 to 38,103 containing cI gene, $P_R$ promoter and a part of cII gene and HaeIII-BglII fragment of bases 35,468 to 35,716 containing $P_L$ promoter, is inserted between PstI site and BamHI site repaired with DNA polymerase I of pBR322. The cI gene in pMY12-6 is the mutant cI857 and therefore shows temperature sensitivity.

About 4 μg of pMY12-6 plasmid DNA (about 4.6 Kb) was dissolved in 40 μl of a buffer solution consisting of 10 mM Tris-HCl (pH 7.5), 100 mM NaCl, 7 mM MgCl$_2$ and 6 mM 2-mercaptoethanol (referred to as "Y-100 buffer solution" hereinafter) and 8 units of BamHI was added. Digestion reaction was carried out at 37° C. for 2 hours. After extraction with phenol and chloroform and precipitation with ethanol, the DNA fragment was dissolved in 40 μl (total volume) of a buffer solution consisting of 50 mM Tris-HCl (pH 7.6), 7 mM MgCl$_2$, 6 mM 2-mercaptoethanol, 0.25 mM dATP, 0.25 mM dCTP, 0.25 mM dGTP and 0.25 mM dTTP (referred to as "DNA polymerase I buffer solution" hereinafter). Then, 6 units of *Escherichia coli* DNA polymerase I· Klenow fragment (product of Bethesda Research Laboratories, the same shall apply hereinafter) was added. Reaction was carried out at 15° C. for 2 hours to change the 5'-protruding end formed by BamHI digestion to a blunt end. The reaction was stopped by phenol extraction, and after chloroform extraction and ethanol precipitation, the DNA fragment was dissolved in 40 μl (total volume) of Y-50 buffer solution and 8 units of PstI was added. Digestion reaction was carried out at 37° C. for 2 hours. After heat treatment at 65° C. for 10 minutes, purification was carried out by low-gelling-temperature agarose gel electrophoresis to obtain a DNA fragment of about 1.35 Kb containing cI gene and $P_R$ and $P_L$ promoters.

Then, about 5 μg of pKYP100 plasmid DNA [T. Nishi, et al.: DNA 2, 265-273 (1983)] having trp portable promoter was digested at 37° C. for 2 hours with 10 units of XhoI in 40 μl of Y-100 buffer solution. After phenol and chloroform extraction and ethanol precipitation, the DNA fragment was dissolved in 40 μl (total volume) of DNA polymerase I buffer solution and 6 units of *Escherichia coli* DNA polymerase I· Klenow fragment was added. Reaction was carried out at 15° C. for 2 hours to change the 5'-protruding end formed by XhoI digestion to a blunt end. The reaction was stopped by phenol extraction, and after chloroform extraction and ethanol precipitation, the DNA fragment was dissolved in 40 μl (total volume) of Y-50 buffer solution. 10 units of PstI was added and reaction was carried out at 37° C. for 2 hours. After heat treatment at 65° C. for 10 minutes, the larger DNA fragment containing trp promoter (about 3.7 Kb) was purified by low-gelling-temperature agarose gel electrophoresis.

About 0.1 μg of the DNA fragment of about 1.35 Kb derived from pMY12-6 and obtained above and the DNA fragment of about 3.7 Kb derived from pKYP100 and obtained above were ligated at 4° C. for 18 hours with 2 units of T4 DNA ligase in 20 μl of T4 DNA ligase buffer solution.

*Escherichia coli* MP347 [F−lacZamY14 trpam8 gal strA (λ bio252 cI857 ΔH1)] (FERM BP-408) was transformed with the thus obtained recombinant plasmid DNA by the method of Cohen, et al. to obtain a tetracycline (Tc) resistant strain. Plasmid DNA was isolated from the transformant and its structure was analyzed to recognize that plasmid pP$_L$T2 in IP$_L$T2 had the desired structure.

*Escherichia coli* strains carrying pMY12-6 and pP$_L$T2 have been deposited with the FERM as *Escherichia coli* IMY12-6 (FERM BP-409) and *Escherichia coli* IP$_L$T2 (FERM BP-407), respectively.

(b) Construction of plasmid vector pP$_L$T4 carrying P$_L$-P$_{trp}$ tandem promoter P$_L$-P$_{trp}$ tandem promoter formed by removing the P$_R$ promoter and a part of the cII gene from P$_R$-P$_L$-P$_{trp}$ tandem promoter was inserted in a plasmid carrying an ampicillin (Ap) resistance gene and a Tc resistance gene so as not to lose both resistances to obtain plasmid expression vector pP$_L$T4 by the following method.

About 5 μg of pP$_L$T2 plasmid DNA was digested at 37° C. for 2 hours with 10 units of BglII in 50 μl of Y-100 buffer solution. Then, after phenol and chloroform extraction and ethanol precipitation, the DNA fragment was dissolved in 40 μl of DNA polymerase I buffer solution and 6 units of *Escherichia coli* DNA polymerase I· Klenow fragment was added. Reaction was carried out at 15° C. for 2 hours to change the 5'-protruding end formed by BglII digestion to a blunt end. Reaction was stopped by phenol extraction, and after chloroform extraction and ethanol precipitation, the DNA fragment was dissolved in 40 μl (total volume) of Y-100 buffer solution. 10 units of BamHI was added and digestion reaction was carried out at 37° C. for 2 hours. After heat treatment at 65° C. for 10 minutes, a plasmid DNA fragment of about 0.7 Kb containing P$_L$-P$_{trp}$ tandem promoter was purified by low-gelling-temperature agarose gel electrophoresis. Then, about 5 μg of pKYP100 plasmid DNA was digested at 37° C. for 2 hours with 10 units of XhoI in 50 μl of Y-100 buffer solution. After phenol and chloroform extraction and ethanol precipitation, the DNA fragment was dissolved in 40 μl (total volume) of DNA polymerase I buffer solution. 6 units of *Escherichia coli* DNA polymerase I· Klenow fragment was added and reaction was carried out at 15° C. for 2 hours to change the 5'-protruding end formed by XhoI digestion to a blunt end. Reaction was stopped by phenol extraction, and after chloroform extraction and ethanol precipitation, the DNA fragment was dissolved in 40 μl (total volume) of Y-100 buffer solution. 10 units of BamHI was added and digestion reaction was carried out at 37° C. for 2 hours. After heat treatment at 65° C. for 10 minutes, the larger plasmid DNA fragment of about 4.0 Kb was purified by low-gelling-temperature agarose gel electrophoresis. About 0.05 μg of the DNA fragment of about 0.7 Kb derived from pP$_L$T2 and obtained above and 0.1 μg of the DNA fragment of about 4.0 Kb derived from pKYP100 and obtained above were ligated at 4° C. for 18 hours with 2 units of T4 DNA ligase in 20 μl of T4 DNA ligase buffer solution.

*Escherichia coli* MP347 was transformed with the recombinant plasmid DNA thus obtained to obtain Ap resistant strains. A Tc resistant strain was selected from the Ap resistant strains and a plasmid DNA was isolated. Its structure was analyzed to recognize that plasmid pP$_L$T4 in IP$_L$T4 had the desired structure.

*Escherichia coli* strain containing pP$_L$T4 has been deposited with the FERM as *Escherichia coli* IP$_L$T4 (FERM BP-406).

REFERENCE EXAMPLE 2

Construction of pTAC10 plasmid carrying tacI promoter (a) Construction of pKYP6 and pKYP30 which carry a DNA fragment containing only "−35" region of trp promoter pKYP6 plasmid (about 7.35 Kb) carrying a DNA fragment containing only "−35" region of trp promoter was constructed from pKYP1 plasmid carrying a part of *Escherichia coli* trp operon (Japanese Published Unexamined Patent Application No. 213193/81) and plasmid pBR325 according to almost the same method as described in Example 1 (b) of the above application. Plasmid pKYP6 has the structure wherein EcoRI-TaqI DNA fragment (about 2.6 Kb) containing only the "−35" region of the trp promoter and derived from pKYP1 is inserted between EcoRI site and ClaI site of plasmid pBR325 (refer to FIG. 5).

Then, about 10 μg of pKYP6 plasmid DNA was digested at 37° C. for 2 hours with 20 units of PvuII and 20 units of HindIII in 50 μl of Y-50 buffer solution. After heat treatment at 65° C. for 10 minutes, a DNA fragment (about 240 bp) containing the "−35" region of the trp promoter was purified by low-gelling-temperature agarose gel electrophoresis.

Separately, about 5 μg of pBR322 plasmid DNA was dissolved in 50 μl of Y-100 buffer solution. 10 units of EcoRI was added and digestion reaction was carried out at 37° C. for 2 hours. Then, after phenol and chloroform extraction and ethanol precipitation, the DNA fragment was dissolved in 40 μl (total volume) of DNA polymerase I buffer solution. 6 units of *Escherichia coli* polymerase I· Klenow fragment was added and reaction was carried out at 15° C. for 2 hours to change the 5'-protruding end formed by EcoRI digestion to a blunt end. Reaction was stopped by phenol extraction, and after chloroform extraction and ethanol precipitation, the DNA fragment was dissolved in 50 μl of Y-50 buffer solution. 10 units of HindIII was added and digestion reaction was carried out at 37° C. for 2 hours. After heat treatment at 65° C. for 10 minutes, the larger plasmid DNA fragment (about 4.3 Kb) was purified by low-gelling-temperature agarose gel electrophoresis.

About 0.02 μg of the DNA fragment of about 240 bp derived from pKYP6 and obtained above, about 0.1 μg of the DNA fragment of about 4.3 Kb derived from pBR322 and obtained above, and 2 pmoles of 5'-phosphorylated EcoRI linker (GGAATTCC: product of Collaborative Research, Inc.) were ligated at 4° C. for 18 hours with 2 units of T4 DNA ligase in 20 μl of T4 DNA ligase buffer solution.

*Escherichia coli* K294 [F− hsdR− hsdM+ endoI− thi] [ATCC31446, K. Backman, et al.: Proc. Natl. Acad. Sci., USA 73, 4174 (1976)] was transformed with the thus obtained recombinant plasmid DNA to obtain an Ap resistant strain. Plasmid DNA was isolated from the transformant and its structure was analyzed to recognize that plasmid pKYP30 in IKYP30 strain had the desired structure (refer to FIG. 5).

(b) Construction of plasmid pTAC10 carrying tacI promoter

As the source of "−10" region of lac promoter and lac operator which are components of tacI promoter, plasmid pLACI was used. Plasmid pLACI has the structure wherein AluI-AluI fragment of 95 bp containing lacUV5 promoter is inserted between EcoRI site and PvuII site of plasmid pBR322 (refer to FIG. 5). Since religation of AluI end and PvuII end forms the base sequence CAGCTG, the religated region can be recleaved with PvuII. BamHI site derived from BamHI linker exists upstream from lac promoter (refer to FIG. 5). The lacUV5 promoter is described in the reference W. S. Reznikoff, et al.: "The operon" , J. H. Miller and W. S. Reznikoff ed, Cold Spring Harbor Laboratory, New York, 1978, p221].

About 10 μg of pLACl plasmid DNA was dissolved in 50 μof a buffer solution consisting of 10 mM Tris-HCl (pH 7.5), 10 mM NaCl, 7 mM MgCl$_2$ and 6 mM 2-mercaptoethanol (referred to as "Y-10 buffer solution" hereinafter). 20 units of HpaII and 20 units of PvuII were added and digestion reaction was carried out at 37° C. for 2 hours. After heat treatment at 65° C. for 10 minutes, HpaII-PvuII DNA fragment (55 bp) containing the "−10" region of the lac promoter, the lac operator and the SD sequence of lacZ was purified by polyacrylamide gel electrophoresis [A. M. Maxam, et al.: Proc. Natl. Acad. Sci. USA 74, 560 (1977)].

Then, about 5 μg of plasmid pKYP30 constructed in Reference Example 2 (a) was dissolved in 50 μl of Y-50 buffer solution. 10 units of ClaI (product of Boehringer Mannheim GmbH, the same shall apply hereinafter), 10 units of PvuII and 15 units of BamHI were added and digestion reaction was carried out at 37° C. for 2 hours. After heat treatment at 65° C. for 10 minutes, a DNA fragment of about 2.6 Kb containing the "−35" region of the trp promoter and an Ap resistance gene was purified by low-gelling-temperature agarose gel electrophoresis.

About 10 ng of the DNA fragment of 55 bp derived from pLACl and obtained above and about 50 ng of the DNA fragment of about 2.6 Kb derived from pKYP30 and obtained above were ligated at 4° C. for 18 hours with 2 units of T4 DNA ligase in 20 μl of T4 DNA ligase buffer solution.

*Escherichia coli* JA221 was transformed with the recombinant plasmid DNA thus obtained to obtain an Ap resistant strain. Plasmid DNA was isolated from the transformant and its structure was analyzed to recognize that plasmid pTAC10 in ITAC10 had the desired structure (refer to FIG. 5).

*Escherichia coli* strain containing recombinant plasmid pTAC10 has been deposited with the FERM as *Escherichia coli* ITAC10 (FERM BP-404).

REFERENCE EXAMPLE 3

Construction of recombinant plasmid pGKA2 expressing human IFN-γ

Figure 6A:
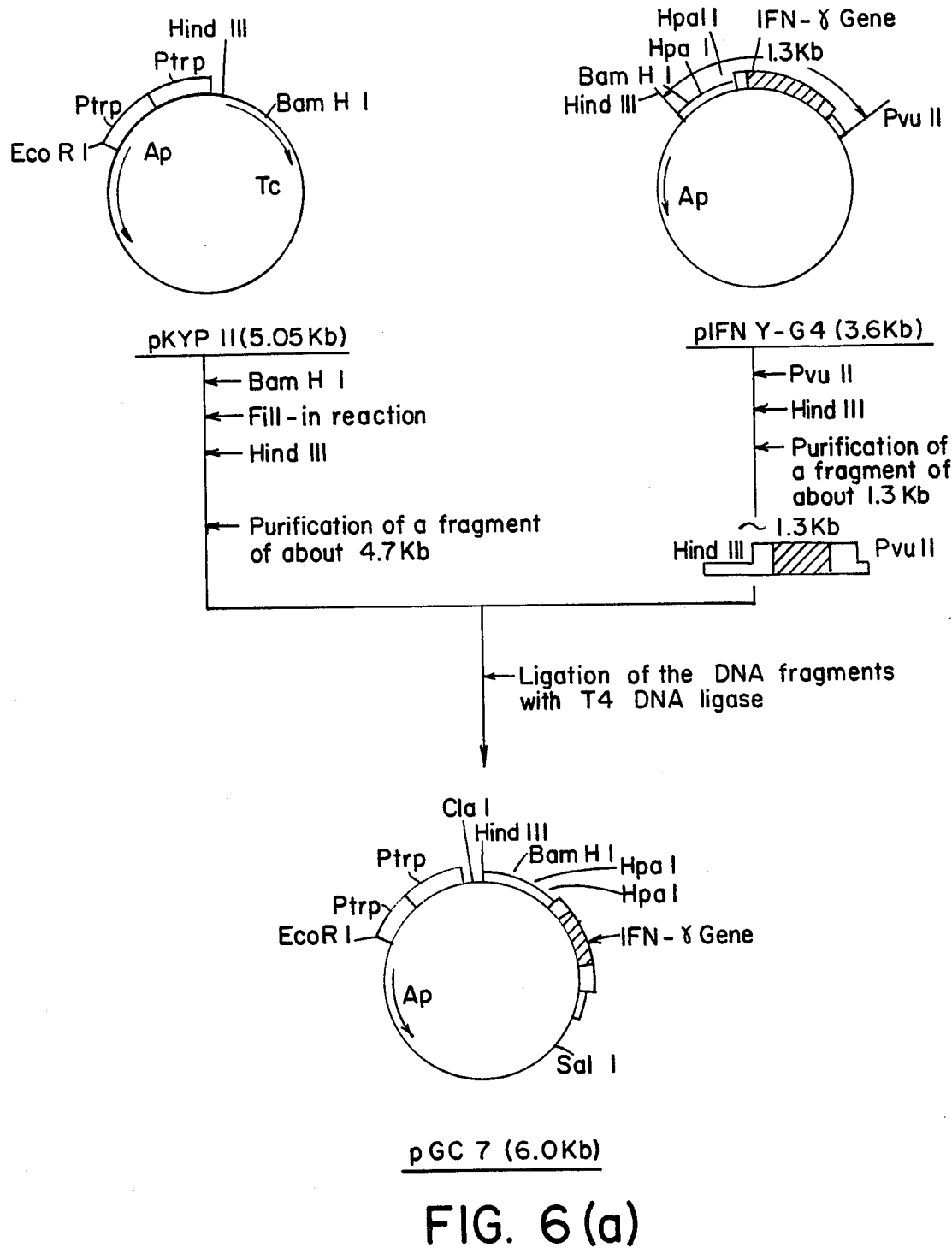
FIG. 6. illustrates the process for constructing pGC7 and pGA2.
Figure 6B:
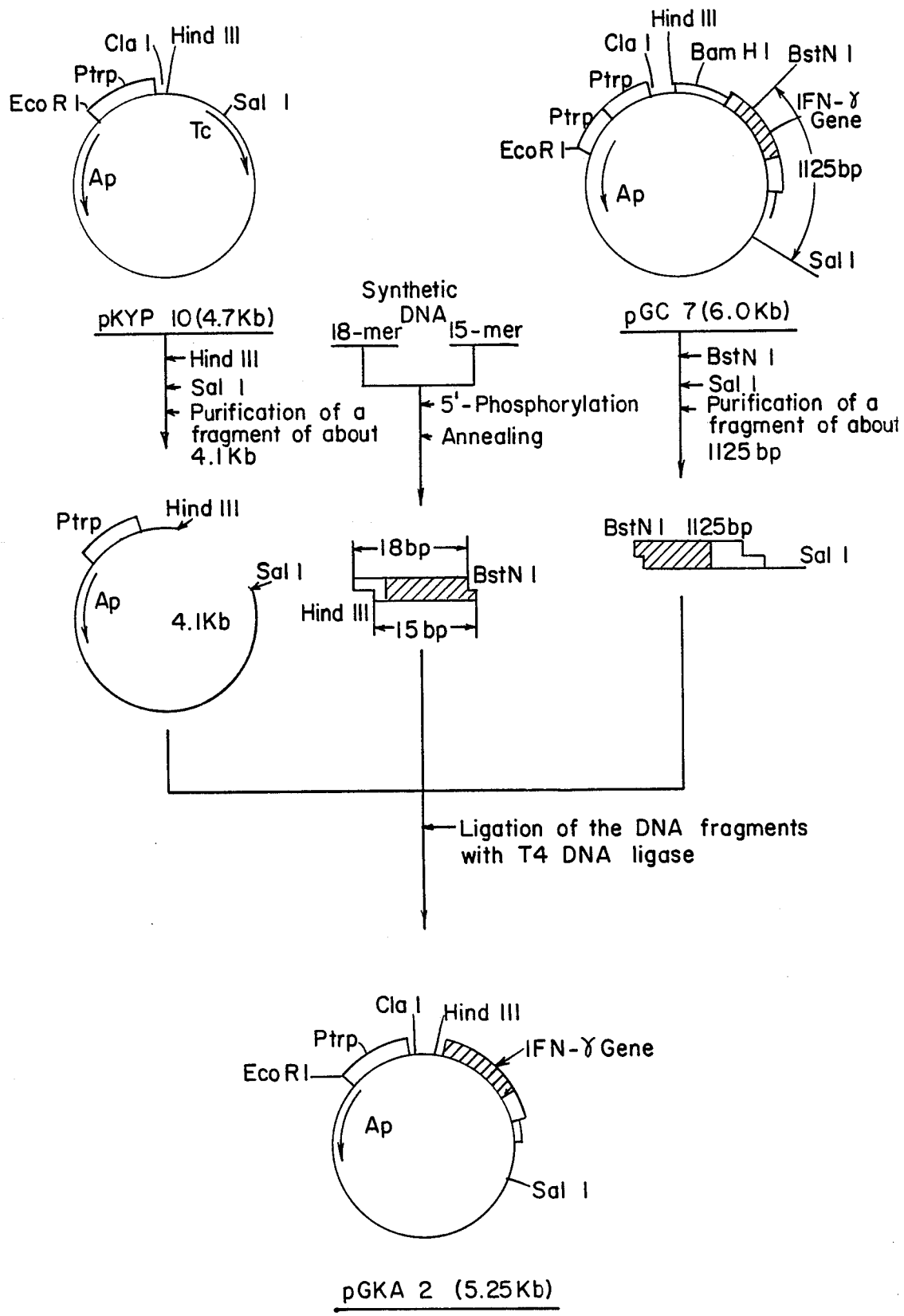

FIG. 6 should be referred to for the following process of construction of plasmids.

(a) Insertion of human IFN-γ DNA into the expression vector pKYP11

In this example, 6 μg of plasmid pIFNY-G4 isolated from ATCC39123 by the isolation method of plasmids described above was dissolved in 50 μl (total volume) of a solution containing 20 mM Tris-HCl (pH 7.5), 10 mM MgCl$_2$, 10 mM dithiothreitol and 50 mM NaCl. Then, 12 units each of restriction enzymes PvuII and HindIII were added and digestion reaction was carried out at 37° C. for 4 hours. The reaction solution was heated at 65° C. for 7 minutes to inactivate the enzymes and subjected to purification by low-gelling-temperature agarose gel electrophoresis to obtain 1.2 μg of a DNA fragment containing human IFN-γ DNA of 1.3 Kb.

Separately, 4 μg of pKYP11 was dissolved in 40 μl (total volume) of a solution containing 20 mM Tris-HCl (pH 7.5), 10 mM MgCl$_2$, 10 mM dithiothreitol and 50 mM NaCl. 3 units of BamHI was added and digestion reaction was carried out at 37° C. for 3 hours. The reaction solution was heated at 65° C. for 5 minutes to inactivate the enzyme. Thereafter, 30 μM each of dATP, dCTP, dGTP and dTTP were added and 8 units of *Escherichia coli* DNA polymerase I (Klenow fragment, product of New England Biolabs, 1 μl) was added. Fill-in reaction was carried out at 15° C. for 1 hour and the reaction solution was heated at 68° C. for 15 minutes to inactivate the DNA polymerase I. 10 units of HindIII was added and digestion reaction was carried out at 37° C. for 3 hours, followed by heating at 65° C. for 5 minutes to inactivate HindIII. The obtained digestion reaction solution of the plasmid pKYP11 was subjected to purification by low-gelling-temperature agarose gel electrophoresis to obtain about 2.5 μg of a DNA fragment of about 4.7 Kb containing P$_{trp}$.

Then, 0.5 μg of the DNA fragment of 1.3 Kb containing human IFN-γ DNA and 10 μg of the DNA fragment of about 4.7 Kb containing Ptrp, which was obtained from the plasmi pKYP11, were dissolved in 20 μl of a solution containing 20 mM Tris-HCl (pH 7.5), 6 mM MgCl$_2$, 5 mM dithiothreitol and 500 μM ATP, and 4 units of T4 DNA ligase (product of New England Biolabs) was added. Ligation reaction was carried out at 4° C. for 18 hours, and *Escherichia coli* HB101 was transformed with the obtained recombinant plasmid mixture by conventional technique to obtain an Ap$^R$ colony. A plasmid, pGC7 illustrated in FIG. 6 was separated from the culture broth of the colony. The structure of pGC7 was confirmed by digestion with HindIII, BamHI, HpaI, SalI, EcoRI and ClaI and agarose gel electrophoresis. *Escherichia coli* strain containing pGC7 has been deposited with the FERM as *Escherichia coli* IGC7 (FERM P-6814, FERM BP-497).

(b) Construction of recombinant plasmid pGKA2

In this example, 6 μg of pGC7 DNA obtained in Reference Example 3(a) was dissolved in 50 μl (total volume) of a solution containing 20 mM Tris-HCl (pH 7.5), 10 mM MgCl$_2$, 10 mM dithiothreitol and 10 mM NaCl, and 12 units of BstNI (product of New England Biolabs) was added. Reaction was carried out at 60° C. for 3 hours. After heating at 65° C. for 5 minutes to inactivate BstNI, 150 mM NaCl and 8 units of SalI were added and digestion reaction was carried out at 37° C. for 3 hours. The reaction solution was again heated at 65° C. for 5 minutes to inactivate SalI and subjected to purification by low-gelling-temperature agarose gel electrophoresis to obtain about 0.8 μg of a DNA fragment of about 1,125 bp containing the most part of the human IFN-γ DNA.

Separately, 3 μg of pKYP10 was dissolved in 40 μl (total volume) of a solution containing 20 mM Tris-HCl (pH 7.5), 10 mM MgCl$_2$, 10 mM dithiothreitol and 100 mM NaCl. 6 units each of HindIII and SalI were added and digestion reaction was carried out at 37° C. for 3 hours. The reaction solution was heated at 65° C. for 5 minutes to inactivate HindIII and SalI and subjected.to purification by low-gelling-temperature agarose gel electrophoresis to obtain about 1.8 μg of a DNA fragment of about 4.1 Kb containing P$_{trp}$.

The N-terminal amino acid of the mature human IFN-γ polypeptide is cystein (Cys). In order to express mature IFN-γ DNA, it is necessary to furnish an initiation codon (ATG) just before the 5'-terminal codon TGT (Cys) and further to adjust the length between the SD-sequence downstream from P$_{trp}$ and ATG to a suitable length of 6–18 bp. Therefore, the following DNA linker was synthesized.

Two single chain DNAs of 18-mer and 15-mer were synthesized by a conventional triester method [R. Crea, et al.: Proc. Natl. Acad. Sci., 75, 5765 (1978)]. Then, 2 μg each of the 18-mer and 15-mer DNAs were dissolved in 20 μl (total volume) of a solution containing 50 mM Tris-HCl (pH 7.5), 10 mM MgCl$_2$, 5 mM dithiothreitol, 0.1 mM EDTA and 1 mM ATP. 30 units of T4 polynucleotide kinase (product of Boehringer Mannheim GmbH) was added and phosphorylation reaction was carried out at 37° C. for 60 minutes.

Then, 2 μg each of phosphorylated 18-mer and 15-mer DNAs were mixed and the mixture was heated at 70° C. for 5 minutes and allowed to stand at room temperature for annealing to obtain the DNA linker having the structure given above.

0.4 μg of the BstNI - SalI fragment of 1,125 bp obtained above and derived from pGC7 and 1.0 ug of the DNA fragment of 4.1 Kb obtained by digestion of the expression vector pKYP10 with HindIII and SalI were dissolved in 25 μl (total volume) of a solution containing 20 mM Tris-HCl (pH 7.5), 6 mM MgCl$_2$, 5 mM dithiothreitol and 500 uM ATP. About 0.1 μg of the DNA linker mentioned above was added to the mixture, followed by addition of 6 units of T4 DNA ligase.

Ligation reaction was carried out at 4° C. for 17 hours. *Escherichia coli* HB101 was transformed using the obtained recombinant plasmid mixture by conventional technique to obtain an Ap^R colony. A plasmid, pGKA2 illustrated in FIG. 6 was isolated from the culture broth of the colony. The structure of pGKA2 was confirmed by digestion with EcoRI, ClaI, HindIII, BstNI and SalI and agarose gel electrophoresis. It was confirmed by the method of Maxam-Gilbert [A. M. Maxam, et al.: Proc. Natl. Acad. Sci., 74, 560 (1977)] that the base sequence from the SD-sequence (AAGG) to the initiation codon (ATG) in the plasmid pGKA2 was "AAGG GTATCGATAAGCTTATG".

The human IFN-γ DNA in pGKA2 is different from known DNAs in that the DNA has RsaI site and the ninth amino acid of the human IFN-γ polypeptide enooded by the DNA is glutamine(Gln).

Further, the synthesized DNA used above is different from the one used by P. W. Gray, et al. having the following structure:

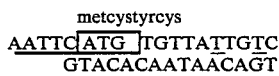

metcystyrcys
AATTC ATG TGTTATTGTC
      GTACACAATAACAGT in the underlined parts. Thus, pGKA2 has a restriction site for BstNI, CCAGG, in the DNA region coding for human IFN-γ and this feature also distinguishes pGKA2 from known plasmids. Furthermore, the length and structure between the SD sequence and ATG are important because of influence on the expression of proteins in *Escherichia coli*. The base sequence between the SD-sequence and ATG in pGKA2 is apparently different from that in the known recombinant plasmid pIFN-γ trp48 (P. W. Gray, et al.).

*Escherichia coli* strain containing pGKA2 has been deposited with the FERM as *Escherichia coli* IGKA2 (FERM P-6798, FERM BP-496).

REFERENCE EXAMPLE 4

Figure 7:
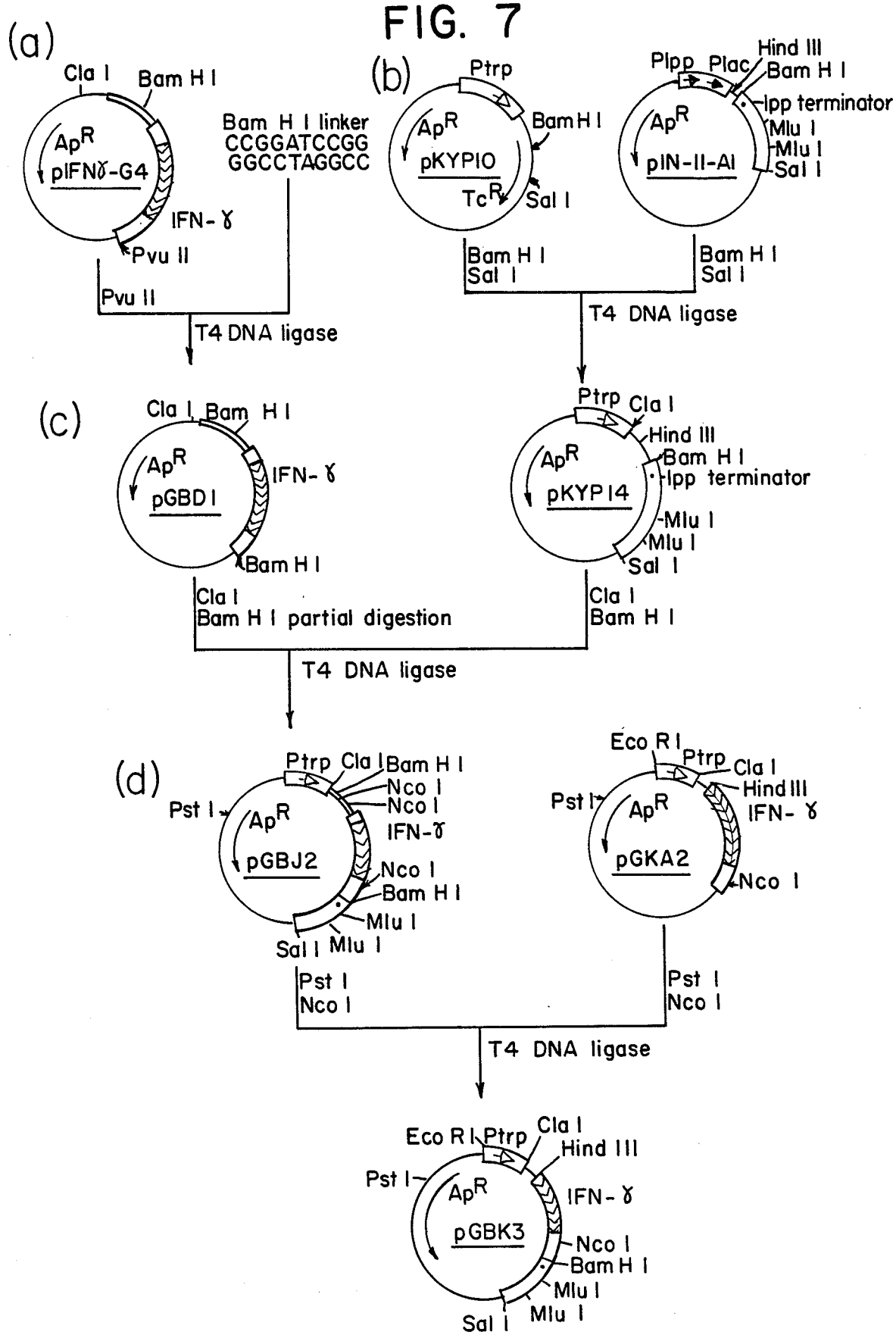
FIG. 7. illustrates the process for constructing pGBK3 and pGTC3.
Figure 7:
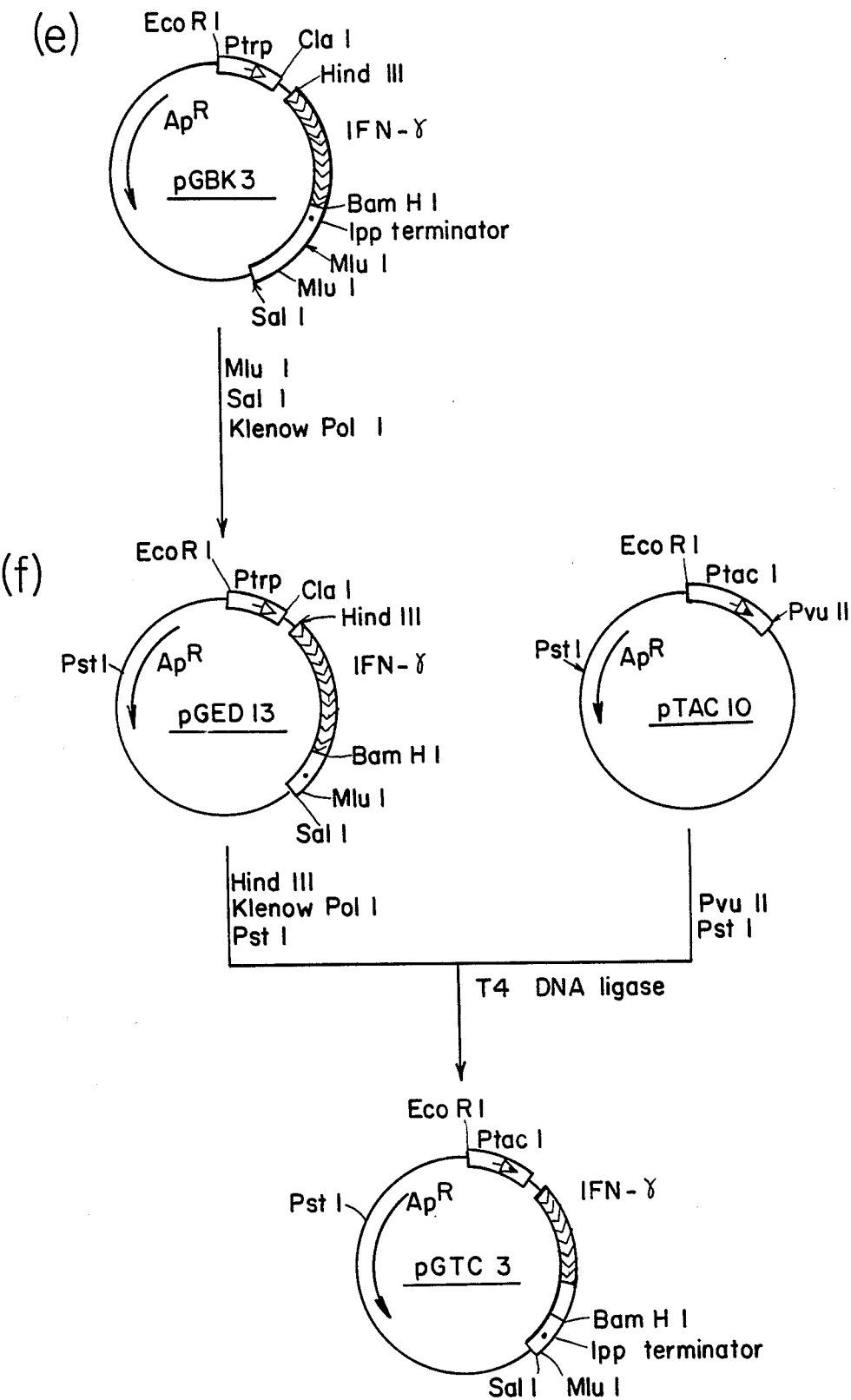

Construction of recombinant plasmid pGTC3 expressing human IFN-γ under the control of tac I promoter As the first step of the construction of recombinant plasmid transcription termination site of *Escherichia coli* lipoprotein (lpp) gene (referred to as lpp terminator hereinafter) was introduced into IFN-γ expressing plasmid pGKA2 according to the following processes (a), (b), (c) and (d) (refer to FIG. 7).

(a) Construction to pGBD1

2 pg of plasmid pIFNγ-G4 (about 3.6 Kb) was dissolved in 20 μl of Y-50 buffer solution and 6 units of PvuII was added. Digestion reaction was carried out at 37° C. for 2 hours and stopped by heat treatment at 65° C. for 10 minutes. 0.1 μg of the digest was subjected to ligation reaction in the presence of 5 pmoles of 5'-phosphorylated Bam HI linker (5'-pCCGGATCCGG-3', product of Collaborative Research, Inc.) at 4° C. for 18 hours with 2 units of T4 DNA ligase in 20 μl of T4 DNA ligase buffer solution.

*Escherichia coli* HB101 was transformed using the recombinant plasmid DNA thus obtained to obtain an Ap resistant colony. Plasmid DNA was isolated from the transformant. The DNA was digested with restriction enzymes such as BamHI and its structure was analyzed to recognize that recombinant plasmid pGBDI wherein BamHI linker was inserted at PvuII site of pIFNλ-G4 was obtained.

(b) Construction of pKYP14

Construction of recombinant plasmid pKYP14 used as the source of lpp terminator is described below.

5 μg of plasmid pKYP10 carrying trp promoter (Japanese Published Unexamined Patent Application No. 110600/83) was dissolved in 40 μl of Y-100 buffer solution. 10 units of BamHI was added and digestion reaction was carried out at 37° C. for 2 hours. Then, 1 μl of Y-100 buffer solution, 2.5 μl of 1M NaCl, 5.5 μl of distilled water and 20 units of SalI were added and reaction was carried out for 37° C. for 2 hours. After heat treatment at 65° C. for 10 minutes, the larger plasmid DNA fragment (about 4.9 Kb) was purified by low-gelling-temperature agarose gel electrophoresis. Separately, 5 μg of plasmid pIN-II-Al carrying lpp terminator [K. Nakamura, et al.: The EMBO Journal 1, 771 (1982)] which is the same as pKEN045 in Japanese Published Unexamined Patent Application No. 140800/82 was digested with BamHI and SalI by the same method as described above. The thus formed HindIII-SalI fragment of about 0.95 Kb containing the lpp terminator was purified.

About 0.1 μg of the DNA fragment derived from pKYP10 and obtained above and about 0.05 μg of the DNA fragment derived from pIN-II-Al and obtained above were ligated at 4° C. for 18 hours with 1 unit of T4 DNA ligase in 20 μl of T4 DNA ligase buffer solution.

*Escherichia coli* HB101 was transformed using the thus obtained recombinant plasmid DNA and plasmid DNA was isolated from the transformant. Its structure was analyzed to recognize that the lpp terminator was inserted downstream from plasmid pKYP14 in IKYP14.

(c) Construction of pGBJ2

Insertion of the lpp terminator downstream from IFN-γ DNA by reoombining recombinant plasmids pGBD1 and pKYP14 obtained in (a) and (b) described above was carried out in the following manner.

5 μg of plasmid pGBDl (about 3.6 Kb) was dissolved in 30 μl of a buffer solution consisting of 10 mM Tris-HCl (pH 7.5), 7 mM MgCl₂ and 6 mM 2-mercaptoethanol (referred to as "Y-0 buffer solution" hereinafter). 10 units of ClaI was added and digestion reaction was carried out at 37° C. for 2 hours. After heat treatment at 65° C. for 10 minutes and cooling in ice, 2 μl of 10-fold concentrated Y-0 buffer solution, 5 μl of 1M NaCl, 12 μl of distilled water and 2.0 unit of BamHI were added. Digestion reaction was carried out at 37° C. for 2 hours. By the reaction, the plasmid DNA was partially digested with BamHI. The thus formed ClaI-BamHI DNA fragment (about 1.3 Kb) containing IFN-γ DNA was purified Separately, 5 μg of plasmid pKYP14 (about 5.8 Kb) containing the lpp terminator was digested with 10 units of ClaI and 20 units of BamHI in 50 μl of Y-50 buffer solution for 2 hours and the larger plasmid DNA fragment of about 5.0 Kb containing the lpp terminator was purified. About 0.1 μg of the DNA fragment derived from pKYP14 and obtained above and about 0.05 μg of the DNA fragment derived from pGBD1 and obtained above were ligated at 4° C. for 18 hours with 1 unit of T4 DNA ligase in 20 μl of T4 DNA ligase buffer solution.

*Escherichia coli* HB101 was transformed using the thus obtained recombinant plasmid. Plasmid DNA was isolated from the transformant and its structure was analyzed to recognize that plasmid pGBJ2 in IGBJ2 strain had the structure wherein the lpp terminator was inserted downstream from IFN-γ DNA.

(d) Construction of pGBK3

Recombinant plasmid pGBJ2 obtained in (c) and IFN-γ expressing plasmid pGKA2 (refer to Reference Example 3) were recombined to construct plasmid pGBK3 having the structure wherein the lpp terminator was inserted downstream from IFN-γ DNA by the following method.

About 5 μg of plasmid pGKA2 (about 5.2 Kb) was dissolved in 30 μl of Y-50 buffer solution. 10 units or more of PstI was added and digestion reaction was carried out at 37° C. for 2 hours. After heat treatment at 65° C. for 10 minutes and cooling in ice, 2 μl of 10-fold concentrated Y-150 buffer solution [100 mM Tris-HCl (pH 7.5), 1.5M NaCl, 70 mM MgCl₂ and 60 mM 2-mercaptoethanol], 3 μl of 1M NaCl, 14 μl of distilled water and 10 units of NcoI (product of New England Biolabs, the same shall apply hereinafter) were added and digestion reaction was carried out at 37° C. for 2 hours. After heat treatment at 65° C. for 10 minutes, a plasmid DNA of about 1.85 Kb containing IFN-γ DNA was purified. About 5 μg of recombinant plasmid pGBJ2 (about 6.4 Kb) obtained above was treated by the same method as in the case of pGKA2 and the thus formed PstI-NcoI plasmid DNA fragment of about 4.7 Kb was purified. About 0.1 μg of the thus obtained DNA fragment derived from pGKA2 and about 0.1 μg of the thus obtained DNA fragment derived from pGBJ2 were ligated at 4° C. for 18 hours with 1 unit of T4 DNA ligase in 20 μl of T4 DNA ligase buffer solution. *Escherichia coli* HB101 was transformed with the thus obtained recombinant plasmid and plasmid DNA was isolated and purified. Its structure was analyzed to recognize that plasmid pGBK3 in IGBK3 had the desired structure.

(e) Construction of pGED13

Plasmid pGED13 wherein a region downstream from the lpp terminator of pGBK3 was removed was constructed by the following procedures in order to construct recombinant plasmid pGTC3 expressing human IFN-γ under the control of tacI promoter from pGBK3 obtained in (d) (refer to FIGS. 7(e) and (f)).

5 μg of pGBK3 plasmid DNA was dissolved in 50 μl of Y-150 buffer solution. 10 units of MluI and 15 units of SalI were added and digestion reaction was carried out at 37° C. for 2 hours. Then, after phenol and chloroform extraction and ethanol precipitation, the DNA fragment was dissolved in 40 μl (total volume) of DNA polymerase I buffer solution. 6 units of *Escherichia coli* DNA polymerase I· Klenow fragment was added and reaction was carried out at 15° C. for 2 hours. After heat treatment at 65° C. for 10 minutes, the larger plasmid DNA fragment (about 5.1 Kb) was purified by low-gelling temperature agarose gel electrophoresis.

The thus obtained DNA fragment of about 5.1 Kb derived from pGBK3 was subjected to ligation reaction was at 4° C. for 18 hours with 1 unit of T4 DNA ligase in 20 μl of T4 DNA ligase buffer solution.

*Escherichia coli* K294 was transformed with the thus obtained recombinant plasmid DNA to obtain and Ap resistant strain. Plasmid DNA was isolated from the transformant and its structure was analyzed to recognize that plasmid pGED13 in IGED13 had the following structure. That is, pGED13 has the structure wherein a region of about 650 bp (between MluI site and SalI site) downstream from the lpp terminator of pGBK3 was removed and since MluI site and SalI site were repaired with DNA polymerase and religated, the religated region can be cleaved with MluI and SalI as illustrated by the following base sequence:

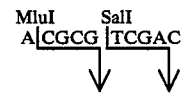

(f) Construction of pGTC3

5 μg of pGED13 plasmid DNA obtained above was dissolved in 50 μl of Y-50 buffer solution. 10 units of HindIII was added and digestion reaction was carried out at 37° C. for 2 hours. Then, after phenol and chloroform extraction and ethanol precipitation, the DNA fragment was dissolved in 40 μl (total volume) of DNA polymerase I buffer solution. 6 units of *Escherichia coli* DNA polymerase I· Klenow fragment was added and reaction was caried out at 15° C. for 2 hours. After phenol and chloroform extraction and ethanol precipitation, the DNA was dissolved in 50 μl (total volume) of Y-50 bufer solution. 10 units of PstI was added and reaction was carried out at 37° C. for 2 hours. After heat treatment at 65° C. for 10 minutes, the larger plasmid DNA fragment (about 4.0 Kb) was purified by low-gelling-temperature agarose gel electrophoresis.

Then, about 5 μg of pTAC10 carrying the tacI promoter and constructed in Reference Example 2 was dissolved in 50 μl of Y-50 buffer solution. 10 units of PvuII and 10 units of PstI were added and digestion reaction was carried out at 37° C. for 2 hours. After heat treatment at 65° C. for 10 minutes, a DNA fragment of about 1.05 Kb containing the tacI promoter was purified using low-gelling-temperature agarose gel electrophoresis.

About 0.1 μg of the thus obtained DNA fragment of about 4.0 Kb derived from pGED13 and about 0.1 μg of the thus obtained DNA fragment of about 1.05 Kb derived from pTAC10 were ligated at 4° C. for 18 hours with 1 unit of T4 DNA ligase in 20 μl of T4 DNA ligase buffer solution.

*Escherichia coli* JA 221 was transformed with the thus obtained recombinant plasmid DNA to obtain an Ap resistant strain. Plasmid DNA was isolated from the transformant and its structure was analyzed to recognize that plasmid pGTC3 in IGTC3 strain had the structure wherein IFN-γ gene was linked downstream from the tacI promoter.

Then, in order to examine the base sequence formed by the ligation of PvuII end of pTAC10 and repaired HindIII end of pGED13, the DNA sequence downstream from the HincII site in the tacI promoter of pGTC3 was determined by the method of Maxam and Gilbert [A. M. Maxam, et al.: Proc. Natl. Acad. Sci. USA. 74, 560 (1977)]. As the result, the base sequence of the linked region between the SD sequence derived from lacZ gene and ATG initiation codon of IFN-γ gene was determined as follows.

```
         linked region
AGGAAACAG|AGCTTATG
  SD         Met
```

*Escherichia coli* strain containing recombinant plasmid pGTC3 has been deposited with the FERM as *Escherichia coli* IGTC3 (FERM BP-402).

What is claim is:

1. A recombinant plasmid having a promoter with a DNA base sequence selected form the group consisting of DNA sequences (A)
GAATTCCTCGAGATCTCTCACCTACCAAACAATGCCCCC
TGCAAAAAATAAATTCATAT
AAAAAACATACAGATAACCATCTGCGGTGATAAATTA
TCTCTGGCGGTGTTGACAATTAA
TCATCGAACTAGTTAACTAGTACGCAAGTTCACGTAA
AAAGGGTATCGATAAGCTT
and
(b)
GAATTCCTCGAGATCTCTCACCTACCAAACAATGCCCC
CCTGCAAAAAATAAATTCATATAA
AAAACATACAGATAACCATCTGCGGTGATAAATTATC
TCTGGCGGTGTTGACAATTAATCAT
CGGCTCGTATAATGTGTGGAATTGTGAGCGGATAACA
ATTTCACACAGGAAACAGCTG.

2. The recombinant plasmid according to claim 1, which is selected from plasmid pGHA2 carried on *Escherichia coli* IGHA2 (FERM BP-400) and plasmid pLECI carried on *Escherichia coli* ILECI (FERM BP-401).

* * * * *

UNITED STATES PATENT AND TRADEMARK OFFICE
CERTIFICATE OF CORRECTION

PATENT NO. : 4,868,125

DATED : September 19, 1989

INVENTOR(S) : TATSUNARI NISHI ET AL.

It is certified that error appears in the above-identified patent and that said Letters Patent is hereby corrected as shown below:

Title Page:
AT [56] REFERENCES CITED

Other Publications,
        "Royama et al., Nucleii Acids Research," should read
        --Aoyama et al., Nucleic Acids Research,--.

COLUMN 6

Table 3, "CGGCTCGTATAATGTGG" should read
        ("-10" region)

--CGGCTCGTATAATGTGTGG--.
        ("-10" region)

Line 56, "of" (second occurrence) should read --or--.

COLUMN 7

Table 4-Continued,

HpaI    -1.
    "TCATCGAACTAGTT | AACTAGTACC" should read
        ("-10" region)

HpaI    -1.
    --TCATCGAACTAGTT | AACTAGTACGC--.
        ("-10" region)

COLUMN 9

Line 64, "[$F^{31}$]" should read --[$F^-$]--.

UNITED STATES PATENT AND TRADEMARK OFFICE
CERTIFICATE OF CORRECTION

PATENT NO. : 4,868,125

DATED : September 19, 1989

INVENTOR(S) : TATSUNARI NISHI ET AL.

It is certified that error appears in the above-identified patent and that said Letters Patent is hereby corrected as shown below:

COLUMN 10

Line 37, "(AAGG-" should read --(AAGG---.

COLUMN 11

Line 50, "hsdR hsdM+⁻trpE5" should read
--hsdR⁻ hsdM⁺ trpE5--.

COLUMN 12

Line 39, "ligaled" should read --ligated--.

COLUMN 13

Line 23, "FIG. 4," should read --FIG. 4.--.
Line 34, "PstIBglII fragment" should read
--PstI-BglII fragment--.

COLUMN 14

Line 26, "[F⁻lacZamY14 trpam8 gal" should read
--[F⁻lacZamY14 trpam8 gal--.
Line 27, "strA (λbio252 cI857 ΔH1)]" should read
--strA (λbio252 cI857 ΔH1)]--.

COLUMN 16

Line 40, "50 μof" should read --50 μℓ of--.

UNITED STATES PATENT AND TRADEMARK OFFICE
CERTIFICATE OF CORRECTION

PATENT NO. : 4,868,125

DATED : September 19, 1989

INVENTOR(S) : TATSUNARI NISHI ET AL

It is certified that error appears in the above-identified patent and that said Letters Patent is hereby corrected as shown below:

COLUMN 17

Line 53, "10 µg" should read --1.0 µg--.
    Line 55, "plasmi pKYP11," should read --plasmid pKYP11,--.

COLUMN 18

Line 60, "1.0 ug" should read --1.0 µg--.
    Line 66, "500 uM ATP." should read --500 µM ATP.--.

COLUMN 19

Line 17, "enooded" should read --encoded--.
    Line 51, "to" should read --of--.
    Line 53, "2 pg" should read --2 µg--.

COLUMN 20

Line 14, "for" (first occurrence) should read --at--.
    Line 41, "reoombining" should read --recombining--.
    Line 57, "purified" should read --purified.--.

COLUMN 21

Line 49, "(f)." should read --(f)).--.
    Line 64, "was" should be deleted.
    Line 67, "and" should read --an--.

UNITED STATES PATENT AND TRADEMARK OFFICE
CERTIFICATE OF CORRECTION

PATENT NO.  : 4,868,125
DATED       : September 19, 1989
INVENTOR(S) : TATSUNARI NISHI ET AL.

It is certified that error appears in the above-identified patent and that said Letters Patent is hereby corrected as shown below:

COLUMN 22

Line 27, "caried" should read --carried--.
    Line 30, "buffer" should read --buffer--.

COLUMN 23

Line 10, "What is claim is:" should read --What is claimed is:--.
    Line 12, "form" should read --from--.

COLUMN 24

Line 7, "(b)" should read --(B)--.

Signed and Sealed this

Twenty-eighth Day of July, 1992

Attest:

DOUGLAS B. COMER

Attesting Officer     Acting Commissioner of Patents and Trademarks